(12) United States Patent
Gordon et al.

(10) Patent No.: US 8,182,529 B2
(45) Date of Patent: May 22, 2012

(54) PERCUTANEOUS MITRAL VALVE ANNULOPLASTY DEVICE DELIVERY METHOD

(75) Inventors: Lucas S. Gordon, Issaquah, WA (US);
Mark L. Mathis, Fremont, CA (US);
Gregory Nieminen, Bothell, WA (US);
Leonard Kowalsky, Bothell, WA (US);
Ryan Braxtan, Snoquamine, WA (US);
Brian J. Doll, Sammamish, WA (US)

(73) Assignee: Cardiac Dimensions, Inc., Kirkland, WA (US)

( * ) Notice: Subject to any disclaimer, the term of this patent is extended or adjusted under 35 U.S.C. 154(b) by 1971 days.

(21) Appl. No.: 10/945,855

(22) Filed: Sep. 20, 2004

(65) Prior Publication Data

US 2005/0119673 A1    Jun. 2, 2005

Related U.S. Application Data

(63) Continuation-in-part of application No. 10/313,914, filed on Dec. 5, 2002, now Pat. No. 7,316,708, and a continuation-in-part of application No. 10/331,143, filed on Dec. 26, 2002, now Pat. No. 6,793,673.

(51) Int. Cl.
*A61F 2/24* (2006.01)
*A61F 2/06* (2006.01)
(52) U.S. Cl. ............ 623/2.11; 606/213; 623/1.11
(58) Field of Classification Search ............ 623/2.1, 623/1.11–1.54, 2.11–2.42; 606/1, 108, 113, 606/127, 144, 213, 110, 114, 128, 190–200
See application file for complete search history.

(56) References Cited

U.S. PATENT DOCUMENTS

| 3,974,526 A | 8/1976 | Dardik et al. |
| 3,995,623 A | 12/1976 | Blake et al. |
| 4,055,861 A | 11/1977 | Carpentier et al. |
| 4,164,046 A | 8/1979 | Cooley |
| 4,485,816 A | 12/1984 | Krumme |
| 4,550,870 A | 11/1985 | Krumme et al. |
| 4,588,395 A | 5/1986 | Lemelson |

(Continued)

FOREIGN PATENT DOCUMENTS

EP    0893133 A1    1/1999

(Continued)

OTHER PUBLICATIONS

Gray, H. Anatomy of the Human Body. The Systemic Veins. Philadelphia: Lea & Febiger, 1918; Bartleby.com. 2000. Available at www.bartleby.com/107/. Accessed Jun. 7, 2006.

(Continued)

*Primary Examiner* — Kathleen Sonnett
(74) *Attorney, Agent, or Firm* — Shay Glenn LLP

(57) ABSTRACT

The invention is a method of delivering and deploying a tissue shaping device in a lumen within a patient, with the tissue shaping device including an anchor. In some embodiments the method includes the steps of: inserting a delivery catheter into the lumen; percutaneously delivering the device to a target site within the lumen through a delivery catheter; operating an actuator to expose an anchor; and operating the actuator to lock the anchor. In other, the method includes the steps of: inserting a delivery catheter into the lumen; moving the device from a cartridge into the delivery catheter; delivering the device to a target site within the lumen; operating an actuator to move the delivery catheter with respect to the anchor to expose the anchor; and expanding the anchor.

52 Claims, 14 Drawing Sheets

U.S. PATENT DOCUMENTS

| | | | |
|---|---|---|---|
| 4,830,023 A | 5/1989 | de Toledo et al. | |
| 5,061,277 A | 10/1991 | Carpentier et al. | |
| 5,099,838 A | 3/1992 | Bardy | |
| 5,104,404 A | 4/1992 | Wolff | |
| 5,250,071 A | 10/1993 | Palermo | |
| 5,261,916 A | 11/1993 | Engelson | |
| 5,265,601 A | 11/1993 | Mehra | |
| 5,350,420 A | 9/1994 | Cosgrove et al. | |
| 5,433,727 A * | 7/1995 | Sideris | 606/213 |
| 5,441,515 A | 8/1995 | Khosravi et al. | |
| 5,449,373 A | 9/1995 | Pinchasik et al. | |
| 5,454,365 A | 10/1995 | Bonutti | |
| 5,458,615 A * | 10/1995 | Klemm et al. | 606/198 |
| 5,474,557 A | 12/1995 | Mai | |
| 5,507,295 A | 4/1996 | Skidmore | |
| 5,507,802 A | 4/1996 | Imran | |
| 5,514,161 A | 5/1996 | Limousin | |
| 5,554,177 A | 9/1996 | Kieval et al. | |
| 5,562,698 A | 10/1996 | Parker | |
| 5,584,867 A | 12/1996 | Limousin et al. | |
| 5,601,600 A | 2/1997 | Ton | |
| 5,676,671 A | 10/1997 | Inoue | |
| 5,733,325 A | 3/1998 | Robinson et al. | |
| 5,741,297 A * | 4/1998 | Simon | 606/213 |
| 5,752,969 A | 5/1998 | Cunci et al. | |
| 5,800,519 A | 9/1998 | Sandock | |
| 5,824,071 A | 10/1998 | Nelson et al. | |
| 5,836,882 A | 11/1998 | Frazin | |
| 5,871,501 A * | 2/1999 | Leschinsky et al. | 606/213 |
| 5,891,193 A | 4/1999 | Robinson et al. | |
| 5,895,391 A | 4/1999 | Farnholtz | |
| 5,899,882 A | 5/1999 | Waksman et al. | |
| 5,908,404 A | 6/1999 | Elliott | |
| 5,928,258 A | 7/1999 | Khan et al. | |
| 5,935,161 A | 8/1999 | Robinson et al. | |
| 5,954,761 A | 9/1999 | Machek et al. | |
| 5,961,481 A * | 10/1999 | Sterman et al. | 604/2 |
| 5,961,545 A | 10/1999 | Lentz et al. | |
| 5,978,705 A | 11/1999 | KenKnight et al. | |
| 5,984,944 A | 11/1999 | Forber | |
| 6,007,519 A | 12/1999 | Rosselli | |
| 6,015,402 A | 1/2000 | Sahota | |
| 6,022,371 A | 2/2000 | Killion | |
| 6,027,517 A | 2/2000 | Crocker et al. | |
| 6,053,900 A | 4/2000 | Brown et al. | |
| 6,077,295 A | 6/2000 | Limon et al. | |
| 6,077,297 A | 6/2000 | Robinson et al. | |
| 6,080,182 A * | 6/2000 | Shaw et al. | 606/213 |
| 6,096,064 A | 8/2000 | Routh | |
| 6,099,549 A | 8/2000 | Bosma et al. | |
| 6,099,552 A | 8/2000 | Adams | |
| 6,129,755 A | 10/2000 | Mathis et al. | |
| 6,171,320 B1 | 1/2001 | Monassevitch | |
| 6,183,512 B1 | 2/2001 | Howanec et al. | |
| 6,190,406 B1 | 2/2001 | Duerig et al. | |
| 6,200,336 B1 | 3/2001 | Pavcnik et al. | |
| 6,210,432 B1 | 4/2001 | Solem et al. | |
| 6,228,098 B1 | 5/2001 | Kayan et al. | |
| 6,241,757 B1 | 6/2001 | An et al. | |
| 6,254,628 B1 | 7/2001 | Wallace et al. | |
| 6,267,783 B1 | 7/2001 | Letendre et al. | |
| 6,275,730 B1 | 8/2001 | KenKnight et al. | |
| 6,312,446 B1 * | 11/2001 | Huebsch et al. | 606/213 |
| 6,334,864 B1 | 1/2002 | Amplatz et al. | |
| 6,342,067 B1 | 1/2002 | Mathis et al. | |
| 6,345,198 B1 | 2/2002 | Mouchawar et al. | |
| 6,352,553 B1 | 3/2002 | van der Burg et al. | |
| 6,352,561 B1 | 3/2002 | Leopold et al. | |
| 6,358,195 B1 | 3/2002 | Green et al. | |
| 6,395,017 B1 | 5/2002 | Dwyer et al. | |
| 6,402,781 B1 | 6/2002 | Langberg et al. | |
| 6,419,696 B1 | 7/2002 | Ortiz et al. | |
| 6,442,427 B1 | 8/2002 | Boute et al. | |
| 6,503,271 B2 | 1/2003 | Duerig et al. | |
| 6,537,314 B2 | 3/2003 | Langberg et al. | |
| 6,562,067 B2 | 5/2003 | Mathis | |
| 6,569,198 B1 | 5/2003 | Wilson et al. | |
| 6,589,208 B2 | 7/2003 | Ewers et al. | |
| 6,599,314 B2 | 7/2003 | Mathis et al. | |
| 6,602,288 B1 | 8/2003 | Cosgrove et al. | |
| 6,602,289 B1 | 8/2003 | Colvin et al. | |
| 6,623,521 B2 | 9/2003 | Steinke et al. | |
| 6,626,899 B2 | 9/2003 | Houser et al. | |
| 6,629,534 B1 | 10/2003 | Dell et al. | |
| 6,629,994 B2 | 10/2003 | Gomez et al. | |
| 6,643,546 B2 | 11/2003 | Mathis et al. | |
| 6,648,881 B2 | 11/2003 | KenKnight et al. | |
| 6,652,538 B2 | 11/2003 | Kayan et al. | |
| 6,656,221 B2 | 12/2003 | Taylor et al. | |
| 6,709,425 B2 | 3/2004 | Gambale et al. | |
| 6,716,158 B2 | 4/2004 | Raman et al. | |
| 6,718,985 B2 | 4/2004 | Hlavka et al. | |
| 6,721,598 B1 | 4/2004 | Helland et al. | |
| 6,723,038 B1 | 4/2004 | Schroeder et al. | |
| 6,733,521 B2 | 5/2004 | Chobotov et al. | |
| 6,743,219 B1 | 6/2004 | Dwyer et al. | |
| 6,764,510 B2 | 7/2004 | Vidlund et al. | |
| 6,773,446 B1 | 8/2004 | Dwyer et al. | |
| 6,776,784 B2 | 8/2004 | Ginn | |
| 6,790,231 B2 | 9/2004 | Liddicoat et al. | |
| 6,793,673 B2 | 9/2004 | Kowalsky et al. | |
| 6,797,001 B2 | 9/2004 | Mathis et al. | |
| 6,800,090 B2 | 10/2004 | Alferness et al. | |
| 6,805,128 B1 | 10/2004 | Pless et al. | |
| 6,827,690 B2 | 12/2004 | Bardy | |
| 6,881,220 B2 | 4/2005 | Edwin et al. | |
| 6,899,734 B2 | 5/2005 | Castro et al. | |
| 6,935,404 B2 | 8/2005 | Duerig et al. | |
| 6,960,229 B2 | 11/2005 | Mathis et al. | |
| 6,964,683 B2 | 11/2005 | Kowalsky et al. | |
| 6,966,926 B2 | 11/2005 | Mathis | |
| 7,152,605 B2 | 12/2006 | Khairkhahan et al. | |
| 2001/0018611 A1 | 8/2001 | Solem et al. | |
| 2001/0041899 A1 | 11/2001 | Foster | |
| 2001/0044568 A1 | 11/2001 | Langberg et al. | |
| 2001/0049558 A1 | 12/2001 | Liddicoat et al. | |
| 2002/0016628 A1 | 2/2002 | Langberg et al. | |
| 2002/0035361 A1 | 3/2002 | Houser et al. | |
| 2002/0042621 A1 | 4/2002 | Liddicoat et al. | |
| 2002/0042651 A1 | 4/2002 | Liddicoat et al. | |
| 2002/0049468 A1 | 4/2002 | Streeter et al. | |
| 2002/0055774 A1 | 5/2002 | Liddicoat | |
| 2002/0065554 A1 | 5/2002 | Streeter | |
| 2002/0087173 A1 | 7/2002 | Alferness et al. | |
| 2002/0095167 A1 | 7/2002 | Liddicoat et al. | |
| 2002/0103532 A1 | 8/2002 | Langberg et al. | |
| 2002/0103533 A1 | 8/2002 | Langberg et al. | |
| 2002/0123802 A1 * | 9/2002 | Snyders | 623/2.18 |
| 2002/0138044 A1 | 9/2002 | Streeter et al. | |
| 2002/0151961 A1 | 10/2002 | Lashinski et al. | |
| 2002/0156526 A1 | 10/2002 | Hlavka et al. | |
| 2002/0161377 A1 * | 10/2002 | Rabkin | 606/108 |
| 2002/0169502 A1 | 11/2002 | Mathis | |
| 2002/0183835 A1 | 12/2002 | Taylor et al. | |
| 2002/0183836 A1 | 12/2002 | Liddicoat et al. | |
| 2002/0183837 A1 | 12/2002 | Streeter et al. | |
| 2002/0183838 A1 | 12/2002 | Liddicoat et al. | |
| 2002/0183841 A1 | 12/2002 | Cohn et al. | |
| 2002/0188170 A1 | 12/2002 | Santamore et al. | |
| 2003/0004572 A1 | 1/2003 | Goble et al. | |
| 2003/0018358 A1 * | 1/2003 | Saadat | 606/232 |
| 2003/0069636 A1 | 4/2003 | Solem et al. | |
| 2003/0078465 A1 | 4/2003 | Pai et al. | |
| 2003/0078654 A1 | 4/2003 | Taylor et al. | |
| 2003/0083538 A1 | 5/2003 | Adams et al. | |
| 2003/0083613 A1 | 5/2003 | Schaer | |
| 2003/0088305 A1 | 5/2003 | Van Schie et al. | |
| 2003/0105520 A1 * | 6/2003 | Alferness et al. | 623/2.36 |
| 2003/0130730 A1 | 7/2003 | Cohn et al. | |
| 2003/0130731 A1 * | 7/2003 | Vidlund et al. | 623/2.37 |
| 2003/0135267 A1 | 7/2003 | Solem et al. | |
| 2003/0144697 A1 | 7/2003 | Mathis et al. | |
| 2003/0171776 A1 | 9/2003 | Adams et al. | |
| 2003/0212453 A1 | 11/2003 | Mathis et al. | |
| 2003/0236569 A1 | 12/2003 | Mathis et al. | |
| 2004/0010305 A1 | 1/2004 | Alferness et al. | |
| 2004/0019377 A1 | 1/2004 | Taylor et al. | |

| | | | |
|---|---|---|---|
| 2004/0039443 A1 | 2/2004 | Solem et al. | |
| 2004/0073302 A1 | 4/2004 | Rourke et al. | |
| 2004/0098116 A1 | 5/2004 | Callas et al. | |
| 2004/0102839 A1 | 5/2004 | Cohn et al. | |
| 2004/0102840 A1 | 5/2004 | Solem et al. | |
| 2004/0111905 A1 | 6/2004 | Gordon et al. | |
| 2004/0127982 A1 | 7/2004 | Machold et al. | |
| 2004/0133220 A1 | 7/2004 | Lashinski et al. | |
| 2004/0133240 A1 | 7/2004 | Adams et al. | |
| 2004/0133273 A1 | 7/2004 | Cox | |
| 2004/0138744 A1 | 7/2004 | Lashinski et al. | |
| 2004/0148019 A1 | 7/2004 | Vidlund et al. | |
| 2004/0148020 A1 | 7/2004 | Vidlund et al. | |
| 2004/0148021 A1 | 7/2004 | Cartledge et al. | |
| 2004/0153147 A1 | 8/2004 | Mathis | |
| 2004/0158321 A1 | 8/2004 | Reuter et al. | |
| 2004/0176840 A1 | 9/2004 | Langberg | |
| 2004/0193191 A1 | 9/2004 | Starksen et al. | |
| 2004/0193260 A1 | 9/2004 | Alferness et al. | |
| 2004/0220654 A1 | 11/2004 | Mathis et al. | |
| 2004/0220657 A1 | 11/2004 | Nieminen et al. | |
| 2004/0243227 A1 | 12/2004 | Starksen et al. | |
| 2004/0249452 A1 | 12/2004 | Adams et al. | |
| 2004/0260342 A1 | 12/2004 | Vargas et al. | |
| 2004/0260384 A1 | 12/2004 | Allen | |
| 2005/0004667 A1 | 1/2005 | Swinford et al. | |
| 2005/0010240 A1 | 1/2005 | Mathis et al. | |
| 2005/0021121 A1 | 1/2005 | Reuter et al. | |
| 2005/0027351 A1 | 2/2005 | Reuter et al. | |
| 2005/0027353 A1 | 2/2005 | Alferness et al. | |
| 2005/0033419 A1 | 2/2005 | Alferness et al. | |
| 2005/0038507 A1 | 2/2005 | Alferness et al. | |
| 2005/0060030 A1 | 3/2005 | Lashinski et al. | |
| 2005/0065598 A1 | 3/2005 | Mathis et al. | |
| 2005/0085903 A1 | 4/2005 | Lau | |
| 2005/0096666 A1 | 5/2005 | Gordon et al. | |
| 2005/0096740 A1 | 5/2005 | Langberg et al. | |
| 2005/0107810 A1 | 5/2005 | Morales et al. | |
| 2005/0137449 A1 | 6/2005 | Nieminen et al. | |
| 2005/0137450 A1 | 6/2005 | Aronson et al. | |
| 2005/0137451 A1 | 6/2005 | Gordon et al. | |
| 2005/0137685 A1 | 6/2005 | Nieminen et al. | |
| 2005/0149179 A1 | 7/2005 | Mathis et al. | |
| 2005/0149180 A1 | 7/2005 | Mathis et al. | |
| 2005/0149182 A1 | 7/2005 | Alferness et al. | |
| 2005/0177228 A1 | 8/2005 | Solem et al. | |
| 2005/0187619 A1 | 8/2005 | Mathis et al. | |
| 2005/0197692 A1 | 9/2005 | Pai et al. | |
| 2005/0197693 A1 | 9/2005 | Pai et al. | |
| 2005/0197694 A1 | 9/2005 | Pai et al. | |
| 2005/0209690 A1 | 9/2005 | Mathis et al. | |
| 2005/0216077 A1 | 9/2005 | Mathis et al. | |
| 2005/0222678 A1 | 10/2005 | Lashinski et al. | |
| 2005/0261704 A1 | 11/2005 | Mathis | |
| 2005/0272969 A1 | 12/2005 | Alferness et al. | |
| 2006/0020335 A1 | 1/2006 | Kowalsky et al. | |
| 2006/0030882 A1 | 2/2006 | Adams et al. | |
| 2006/0041305 A1 | 2/2006 | Lauterjung | |
| 2006/0142854 A1 | 6/2006 | Alferness et al. | |
| 2006/0167544 A1 | 7/2006 | Nieminen et al. | |
| 2006/0191121 A1 | 8/2006 | Gordon | |
| 2006/0271174 A1 | 11/2006 | Nieminen et al. | |
| 2006/0276891 A1 | 12/2006 | Nieminen et al. | |
| 2007/0055293 A1 | 3/2007 | Alferness et al. | |
| 2007/0066879 A1 | 3/2007 | Mathis et al. | |

FOREIGN PATENT DOCUMENTS

| | | | |
|---|---|---|---|
| EP | 0903110 A1 | 3/1999 | |
| EP | 0968688 A1 | 1/2000 | |
| EP | 1050274 A1 | 11/2000 | |
| EP | 1095634 A2 | 5/2001 | |
| GB | 0741604 | 12/1955 | |
| JP | 2754067 | 3/1998 | |
| JP | 2000-308652 | 11/2000 | |
| JP | 2001-503291 | 3/2001 | |
| JP | 2003-503101 | 1/2003 | |
| JP | 2003-521310 | 7/2003 | |
| WO | WO98/48717 | 11/1998 | |
| WO | WO 98/56435 A1 | 12/1998 | |
| WO | WO 00/44313 A1 | 8/2000 | |
| WO | WO 00/60995 A2 | 10/2000 | |
| WO | WO 00/60995 A3 | 10/2000 | |
| WO | WO 00/74603 A1 | 12/2000 | |
| WO | WO 01/00111 A1 | 1/2001 | |
| WO | WO 01/19292 A1 | 3/2001 | |
| WO | WO01/30248 | 5/2001 | |
| WO | WO 01/50985 A1 | 7/2001 | |
| WO | WO 01/54618 A1 | 8/2001 | |
| WO | WO 01/87180 A2 | 11/2001 | |
| WO | WO 02/00099 A2 | 1/2002 | |
| WO | WO 02/01999 A2 | 1/2002 | |
| WO | WO 02/05888 A1 | 1/2002 | |
| WO | WO 02/19951 A1 | 3/2002 | |
| WO | WO 02/34118 A2 | 5/2002 | |
| WO | WO 02/47539 A2 | 6/2002 | |
| WO | WO 02/053206 A2 | 7/2002 | |
| WO | WO 02/060352 A1 | 8/2002 | |
| WO | WO 02/062263 A2 | 8/2002 | |
| WO | WO 02/062270 A1 | 8/2002 | |
| WO | WO 02/062408 A2 | 8/2002 | |
| WO | WO 02/076284 A2 | 10/2002 | |
| WO | WO 02/078576 A2 | 10/2002 | |
| WO | WO 02/096275 A2 | 12/2002 | |
| WO | WO 03/015611 A2 | 2/2003 | |
| WO | WO 03/037171 A2 | 5/2003 | |
| WO | WO 03/049647 A1 | 6/2003 | |
| WO | WO 03049648 A2 | 6/2003 | |
| WO | WO 03/055417 A1 | 7/2003 | |
| WO | WO 03/059198 A2 | 7/2003 | |
| WO | WO 03/063735 A2 | 8/2003 | |
| WO | WO 04/045463 A2 | 6/2004 | |
| WO | WO 2004/084746 | 10/2004 | |
| WO | WO 2005/046531 | 5/2005 | |
| WO | WO 2006/002492 A1 | 1/2006 | |

OTHER PUBLICATIONS

Mark L. Mathis, et al. U.S. Appl. No. 11/279,352, entitled "Mitral Valve Annuloplasty Device with Vena Cava Anchor," filed Apr. 11, 2006.

Heartsite.com. Echocardiogram, 1999; p. 1-4. A.S.M. Systems Inc. Available at: http://www.heartsite.com/html/echocardiogram.html. Accessed Jul. 1, 2005.

Clifton Alferness, et al. U.S. Appl. No. 10/429,225, entitled "Device and method for modifying the shape of a body organ," filed May 2, 2003.

Gary Swinford, et al. U.S. Appl. No. 11/276,082, entitled "Device, System and Method to Affect the Mitral Valve Annulus of a Heart," filed Feb. 13, 2006.

Greg Nieminen, et al. U.S. Appl. No. 10/845,474, entitled "Device and method for modifying the shape of a body organ," filed May 12, 2004.

Greg Nieminen, et al. U.S. Appl. No. 11/275,630, entitled "Tissue Shaping Device," filed Jan. 19, 2006.

Mark Mathis, et al. U.S. Appl. No. 10/994,153, entitled "Body lumen device anchor, device and assembly," filed Nov. 19, 2004.

Papageorgiou, P., et al., "Coronary Sinus Pacing Prevents Induction of Atrial Fibrillation," Circulation 96: 1893-1898, Sep. 16, 1977.

Mathis et al., U.S. Patent Application entitled: "Device and Method for Modifying the Shape of a Body Organ", U.S. Appl. No. 10/429,172, filed May 2, 2003.

Mathis, Mark: U.S. Appl. No. 11/655,710, entitled "Mitral Valve Device Using Conditioned Shape Memory Alloy," filed Jan. 18, 2007.

Mathis et al., U.S. Appl. No. 11/782,490 entitled "Device and method for modifying the shape of a body organ," filed Jul. 24, 2007.

Mathis et al., U.S. Appl. No. 11/782,508, entitled "Device and method for modifying the shape of a body organ," filed Jul. 24, 2007.

Mathis et al., U.S. Appl. No. 11/782,527 entitled "Device and method for modifying the shape of a body organ," filed Jul. 24, 2007.

Mathis et al; U.S. Appl. No. 11/963,417 entitled "Device and method for modifying the shape of a body organ," filed Dec. 21, 2007.

Mathis et al.; U.S. Appl. No. 12/016,054 entitled "Fixed anchor and pull mitral valve device and method," filed Jan. 17, 2008.

Gordon et al.; U.S. Appl. No. 11/971,174 entitled "Medical device delivery system," filed Jan. 8, 2008.

Pai, Suresh; U.S. Appl. No. 60/329,694 entitled "Percutaneous cardiac support structures and deployment means," filed Oct. 16, 2001.

Mathis et al.; U.S. Appl. No. 12/016,054 entitled "Fixed anchor and pull mitrel valve device and method," filed Jan. 17, 2008.

Nieminen et al; U.S. Appl. No. 12/060,781 entitled "Tissue shaping device," filed Apr. 1, 2008.

Hayner et al.; U.S. Appl. No. 12/189,527 entitled "Catheter cutting tool," filed Aug. 11, 2008.

El-Maasarany et al.; The coronary sinus conduit function: Anatomical study (relationship to adjacent structures); http://europace.oxfordjournals.org/cge/content/full/7/5/475.

* cited by examiner

PERCUTANEOUS MITRAL VALVE ANNULOPLASTY DEVICE DELIVERY METHOD

CROSS-REFERENCE

This application is a continuation-in-part application of U.S. patent application Ser. No. 10/313,914, filed Dec. 5, 2002, now U.S. Pat. No. 7,316,708, and U.S. patent application Ser. No. 10/331,143, filed Dec. 26, 2002, now U.S. Pat. No. 6,793,673 which applications are incorporated herein by reference in their entirety and to which applications we claim priority under 35 USC §120.

BACKGROUND OF THE INVENTION

The invention relates generally to percutaneous delivery systems for tissue shaping devices intended to be delivered through a lumen to a site within a vessel of the patient to modify target tissue adjacent to the vessel. In particular, the invention relates to delivery systems for percutaneous mitral valve annuloplasty devices and methods for using the same.

Tissue shaping devices for treating mitral valve regurgitation have been described. See, e.g., U.S. patent application Ser. No. 10/142,637, "Body Lumen Device Anchor, Device and Assembly;" U.S. patent application Ser. No. 10/331,143, "System and Method to Effect the Mitral Valve Annulus of a Heart;" U.S. patent application Ser. No. 10/429,172, "Device and Method for Modifying the Shape of a Body Organ;" and U.S. patent application Ser. No. 10/742,516, "Tissue Shaping Device With Conformable Anchors." These devices are intended to be delivered percutaneously to a site within a patient's coronary sinus and deployed to reshape the mitral valve annulus adjacent to the coronary sinus.

During deployment of such tissue shaping devices one or more anchors may need to be expanded and locked using actuation forces delivered from outside the patient. Thus, the percutaneous delivery and deployment of tissue shaping devices may require the physician to perform remote operations on the device and on the patient through the device. What is needed, therefore, is a delivery system that permits the physician to perform these tasks.

SUMMARY OF THE INVENTION

The present invention provides a tissue shaping delivery system and method. One aspect of the invention provides a method of delivering and deploying a tissue shaping device in a lumen within a patient, the tissue shaping device including an anchor. The method includes the steps of: inserting a delivery catheter into the lumen; percutaneously delivering the device to a target site within the lumen through a delivery catheter; operating an actuator to expose an anchor; and operating the actuator to lock the anchor. The step of operating the actuator to expose the anchor may include the step of operating the actuator to move the delivery catheter proximally and/or distally. The method may also include the step of permitting the anchor to self-expand after exposing the anchor.

In some embodiments the step of operating the actuator to lock the anchor includes the step of engaging the anchor with an actuation force, such as by expanding and locking the anchor. The method may also include the step of applying a proximally directed force on the anchor after locking the anchor. In embodiments in which the tissue shaping device includes a second anchor, the method may also include the step of expanding the second anchor.

In some embodiments in which the tissue shaping device includes a second anchor, the method may also include the step of operating the actuator to expose the second anchor. These embodiments may also include the step of permitting the second anchor to self-expand after exposing the second anchor and/or expanding and locking the second anchor. The step of expanding and locking the second anchor may include the step of operating a second actuator to expand and lock the second anchor. In some embodiments the method includes the step of delivering an imaging contrast agent through the delivery catheter to the treatment site while the tissue treatment device is within the lumen.

In some embodiments the method includes the step of releasing the tissue shaping device from a delivery mechanism. The releasing step may include the step of operating a second actuator to release the tissue shaping device from the delivery mechanism and/or disconnecting a tether from the tissue shaping device, such as by removing a hitch wire from the tissue shaping device.

In some embodiments the method includes the step of recapturing the tissue shaping device into the delivery catheter.

In some embodiments the percutaneously delivering step includes the step of moving the tissue shaping device from a cartridge into the delivery catheter. The cartridge may also be attached to the delivery catheter, such as to a connector extending from the delivery catheter.

Another aspect of the invention provides a method of delivering and deploying a tissue shaping device in a lumen of a patient, with the tissue shaping device including an anchor. The method includes the steps of: inserting a delivery catheter into the lumen; moving the device from a cartridge into the delivery catheter; delivering the device to a target site within the lumen; operating an actuator to move the delivery catheter with respect to the anchor to expose the anchor; and expanding the anchor. In some embodiments the method also includes the step of locking the cartridge onto the delivery catheter. In some embodiments the method also includes the step of loading the tissue shaping device into the cartridge.

In some embodiments the delivery step includes the step of moving a pusher distally to push the device through the delivery catheter. The pusher may be attached to a handle, in which case the delivering step may include the step of moving the handle toward the cartridge. The method may also include the step of engaging the cartridge with the handle. The cartridge may move at least partially into the handle after the engaging step. The engaging step may also include mating the actuator with the cartridge or, in embodiments the actuator is mounted on the cartridge prior to the engaging step, attaching the actuator to the handle. The actuating step may also include the step of rotating the actuator after the engaging step, and the delivering step may include the step of delivering the device substantially to a distal end of the delivery catheter when the cartridge engages the handle.

In some embodiments the expanding step includes the step of permitting the anchor to self-expand. In some embodiments the method includes the step of locking the anchor in an expanded configuration, such as by applying an external actuation force on the anchor by, e.g., operating the actuator to move the delivery catheter distally.

In some embodiments the expanding step includes the step of applying an external actuation force on the anchor, such as by operating the actuator to move the delivery catheter distally. The method may also include the step of applying a proximally directed force on the device after the expanding step, such as by pulling proximally on a tether attached to the device. In embodiments in which the anchor is a distal anchor, the method may include the step operating the actuator to move the delivery catheter proximally to expose a proximal anchor after the applying step.

In embodiments in which the anchor is a distal anchor and the method includes the step of operating the actuator to move the delivery catheter proximally to expose a proximal anchor, the method may also include the step of expanding the proximal anchor (such as by, e.g., applying an external actuation force on the proximal anchor) and perhaps locking the proximal anchor in an expanded configuration. The step of locking the proximal anchor may include the step of applying an external actuation force on the proximal anchor, such as by operating the actuator to move the delivery catheter distally or by operating a second actuator to move a proximal anchor locking device distally. The step of applying an external actuation force on the proximal anchor may include the step of operating the actuator to move the delivery catheter distally or the step of operating a second actuator to move a proximal anchor expansion device distally.

In some embodiments the method includes the step of disengaging the device from a delivery device, such as a by disengaging a tether from the device. The step of disengaging a tether may include the step of disengaging a hitch wire from the device, such as by operating a second actuator to move the hitch wire proximally.

Some embodiments of the method include the step of recapturing the device after the expanding step, such as by operating the actuator to move the delivery catheter distally.

Incorporation by Reference

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

While the invention relates to methods and devices for delivering tissue shaping devices generally, the invention will be described with respect to tissue shaping devices delivered to the coronary sinus of the heart to reshape the mitral valve annulus to treat mitral valve regurgitation. As used herein, "coronary sinus" includes the great cardiac vein as well as the coronary sinus of the heart.

Figure 1:
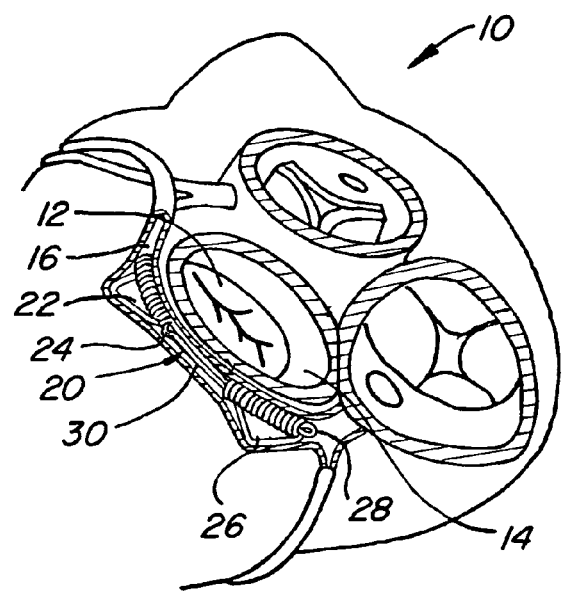
FIG. 1 is a cross-sectional view of a human heart showing a tissue shaping device in the lumen of the coronary sinus.

FIG. 1 shows a cross-section of a human heart 10 with the atria removed to show the mitral valve 12, the mitral valve annulus 14 and the coronary sinus 16. A tissue shaping device 20 in the form of a percutaneous mitral valve annuloplasty device is disposed within the coronary sinus to reshape the mitral valve annulus 14 to provide for improved coaptation of the mitral valve leaflets. As shown, tissue shaping device 20 has an expandable distal anchor 22, a distal anchor lock 24, an expandable proximal anchor 26, a proximal anchor lock 28, and a connector 30 extending between the distal and proximal anchors. Proximal anchor lock 28 has serves as a delivery system attachment mechanism, as explained below.

Figure 2:
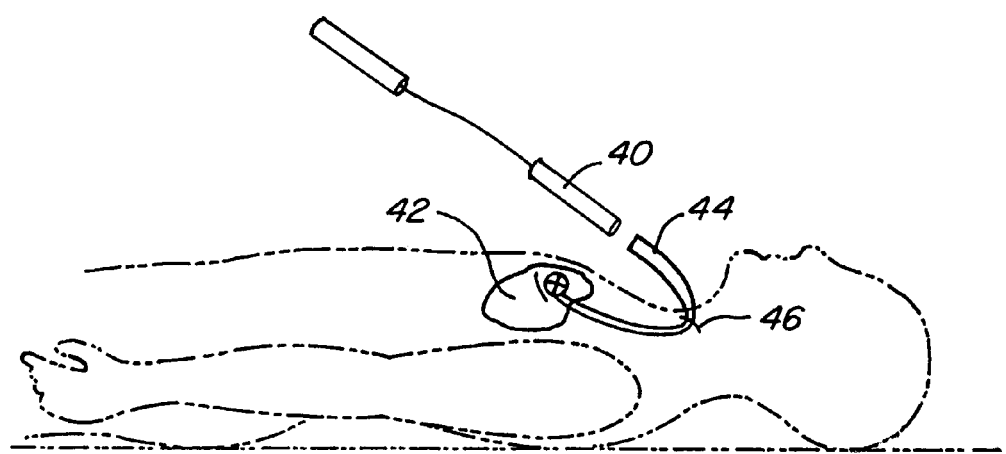
FIG. 2 is a schematic view of a tissue shaping device delivery system according to this invention.

FIG. 2 is a schematic drawing showing the general elements of a delivery system 40 adapted to delivering and deploying a tissue shaping device to a target site within the lumen of a vessel in or around a patient's heart 42. A delivery catheter 44 has been inserted through an opening 46 formed in the patient's jugular vein or other blood vessel and advanced into the heart. Delivery system 40 interacts with delivery catheter 44 to deliver and deploy the tissue shaping device at the target site within the patient.

Figure 3:
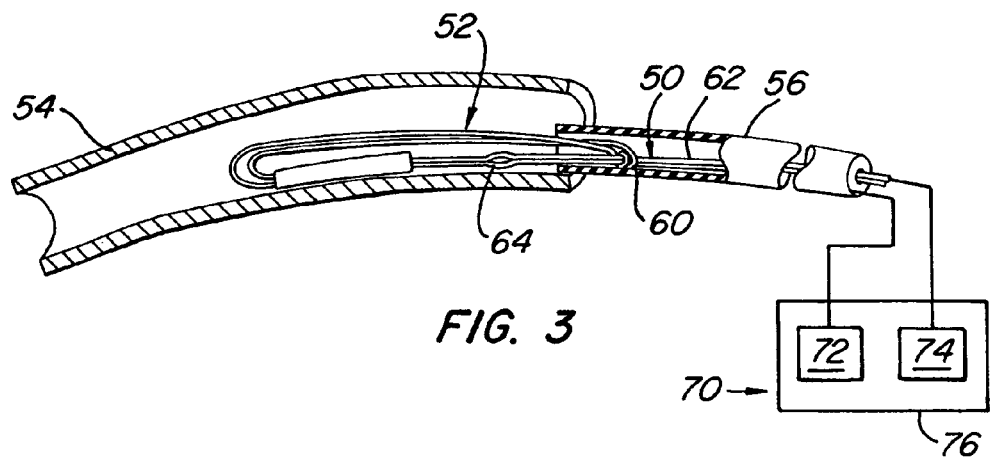
FIG. 3 is a cross-sectional view showing a step in the delivery and deployment of a tissue shaping device according to this invention.

FIGS. 3-6 show steps from the delivery and deployment of a tissue shaping device having at least one anchor similar to the anchors of device 20 of FIG. 1. In FIG. 3, a tissue shaping device 50 has been delivered to a target site within the lumen of a vessel 54 via a delivery catheter 56. FIG. 3 shows an expandable anchor 52 of tissue shaping device 50 beginning to emerge from catheter 56. In this embodiment, this action is due to proximal movement of catheter 56 while device 50 is held stationary. In alternative embodiments, the device could be delivered from the distal end of the catheter by pushing the device distally while holding the catheter stationary or a combination of distal movement of the device and proximal movement of the catheter. Anchor 52 is shown in a collapsed, unexpanded configuration.

A delivery system 70 provides the mechanisms to deliver and deploy device 50 from outside the patient. Actuator 72 and delivery mechanism 74 associated with catheter 56 and device 50, respectively, provide for the relative movement between device 50 and catheter 56. For example, delivery mechanism 74 may be a pusher used to advance device 50 down catheter 56 to the target site shown in FIG. 3, and actuator 72 can be used to pull catheter 56 proximally while delivery mechanism 74 holds device 50 stationary within vessel 54. Actuator 72 and delivery mechanism 74 may be supported by a handle or other housing 76.

Figure 4:
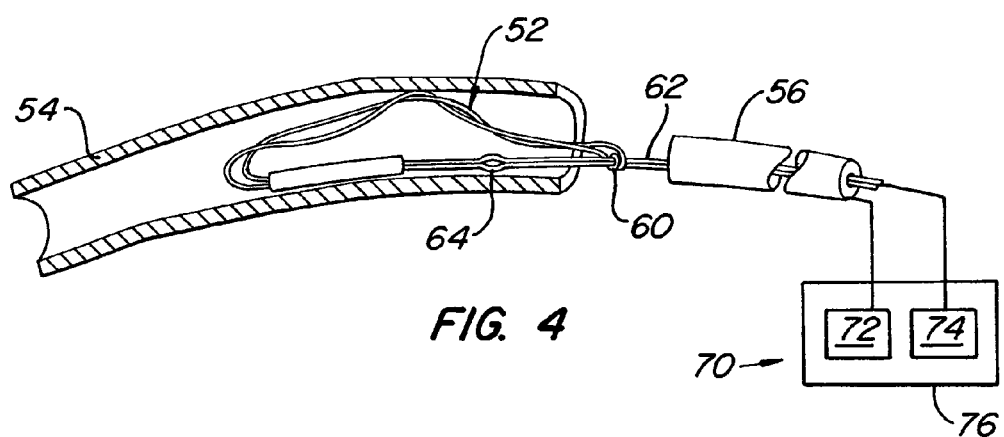
FIG. 4 is a cross-sectional view showing another step in the delivery and deployment of a tissue shaping device according to this invention.

In FIG. 4, catheter 56 has been pulled further proximally by actuator 72 so that anchor 52 is completely outside of catheter 56 and has started to self-expand. In this embodiment, anchor 52 is formed from a shape memory material (such as Nitinol) and has been treated so as to expand upon emergence from the catheter.

Figure 5:
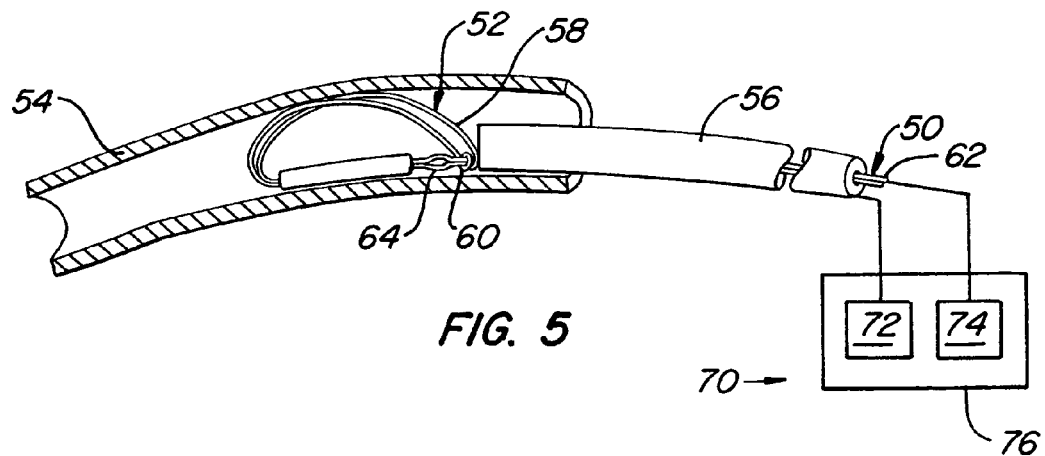
FIG. 5 is a cross-sectional view showing another step in the delivery and deployment of a tissue shaping device according to this invention.
Figure 6:
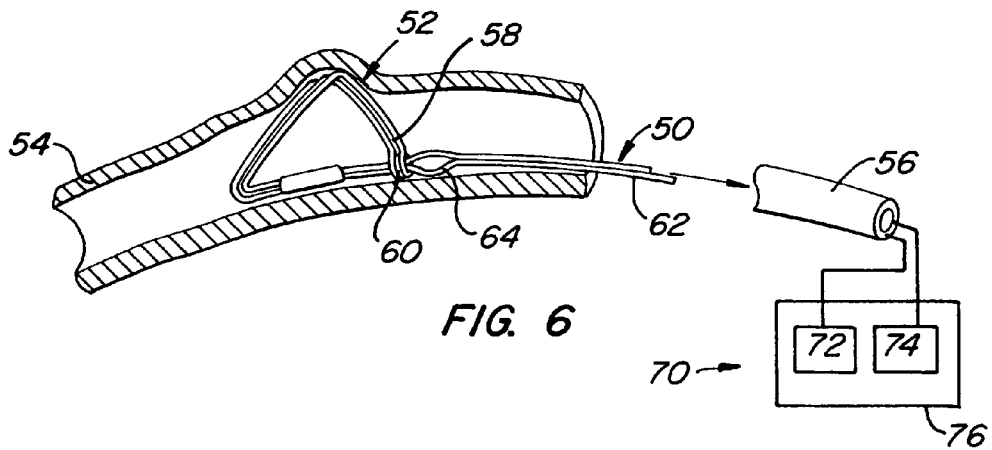
FIG. 6 is a cross-sectional view showing another step in the delivery and deployment of a tissue shaping device according to this invention.

FIGS. 5 and 6 show how the delivery system may be used to further expand and lock anchor 52. Formed in the proximal side 58 of anchor 52 is a loop 60 encircling a proximally extending connector 62. Connector 62 may connect with other elements at the proximal side of device 50, such as a second anchor, depending on device design. As shown in FIG. 5, while delivery mechanism 74 holds device 50 stationary, actuator 72 has moved delivery catheter 56 distally to engage the proximal side 58 of anchor 52 and to move it distally to further expand anchor 52.

As shown in FIG. 6, further distal movement of delivery catheter 56 with respect to device 50 has pushed loop 60 distally over a lock bump 64. Lock bump 64 cams inward in response to the distal force of loop 60, then returns to its prior shape to hold loop 60 distal to lock bump 64. Delivery catheter may then be moved proximally to perform other functions or to be removed from the patient.

Figure 7:
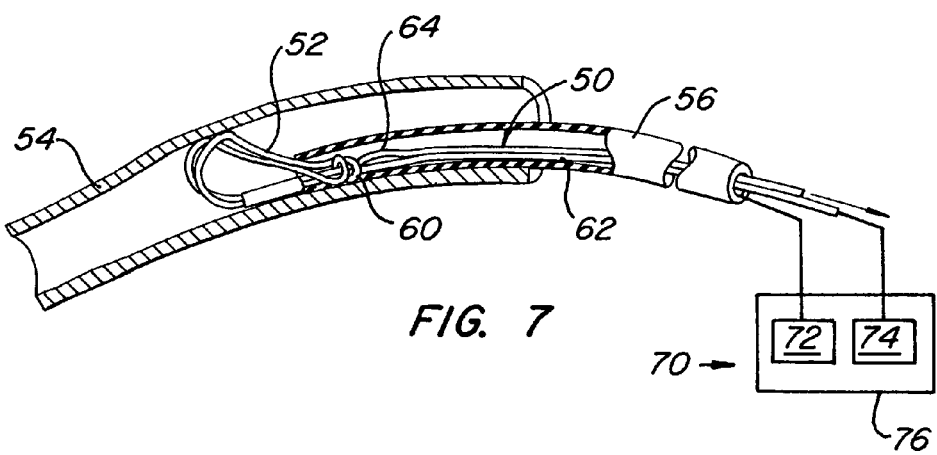
FIG. 7 is a cross-sectional view showing a step in the recapture of a tissue shaping device according to this invention.
Figure 8:
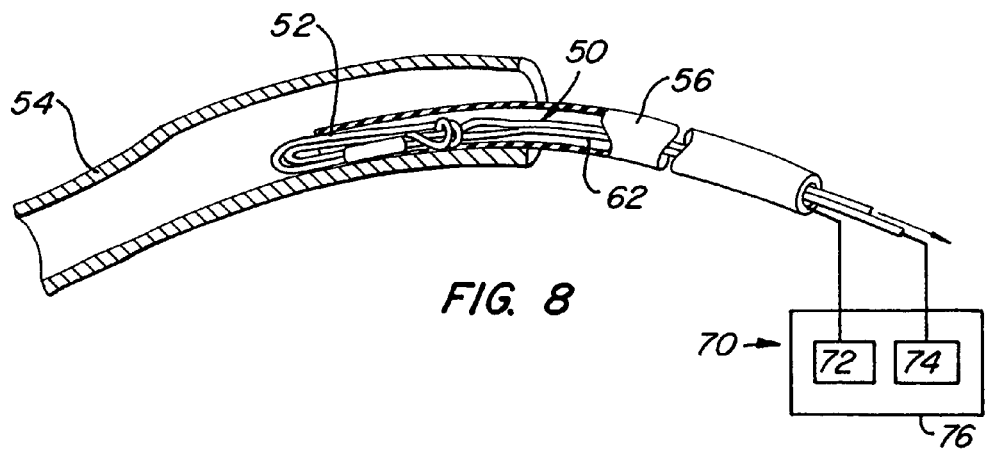
FIG. 8 is a cross-sectional view showing a step in the recapture of a tissue shaping device according to this invention.

After deployment of a tissue shaping device, it may become necessary to reposition the device or to remove the device from the patient. FIGS. 7 and 8 demonstrate the recapture of tissue shaping device 50 back into delivery catheter 56 after delivery and deployment.

In FIG. 7, delivery mechanism 74 holds device 50 stationary while delivery catheter 56 is advanced distally against anchor 52 by actuator 72. The actuation force against anchor 52 collapses the anchor, allowing delivery catheter to recapture the device as shown in FIG. 8. The catheter and device can then be removed from the patient or moved to another target site.

Figure 9:
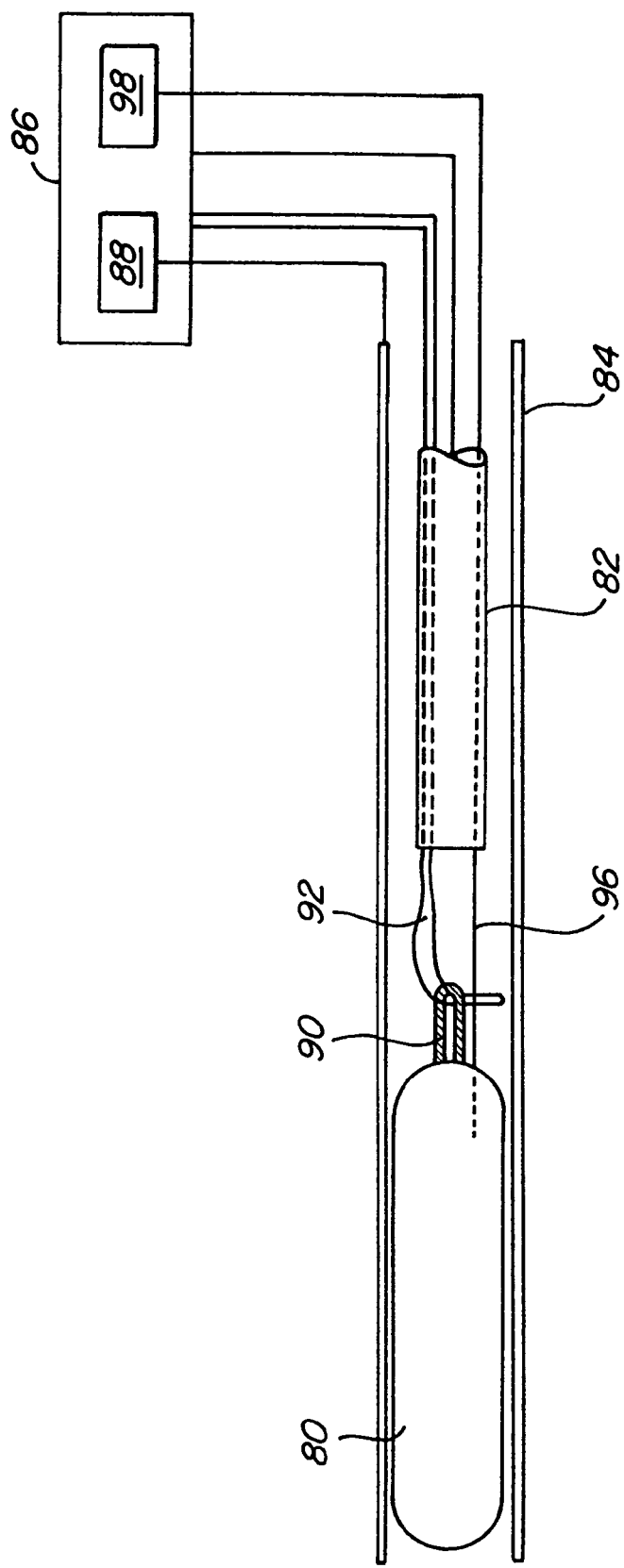
FIG. 9 shows an attachment mechanism for a tissue shaping device delivery system.

FIG. 9 shows an attachment mechanism between a tissue shaping device 80 and a delivery mechanism, such as pusher 82, within a delivery catheter 84. Pusher extends outside of the patient and is attached to a handle or other housing 86, such as through an actuator. Pusher 82 may be operated by an actuator or by the handle itself to advance device 80 distally through catheter 84 or to hold device 80 stationary against a proximal force exerted on device 80, such as when delivery catheter 84 is withdrawn proximally by an actuator 88.

Device 80 has an attachment eyelet 90. A tether 92 extending down pusher 82 has a loop 94 formed at its distal end. The proximal ends of tether 92 are preferably attached to handle 86. Loop 94 extends through eyelet 90, and a hitch wire 96 passes through loop 94 and into the proximal end of device 80 as shown, thereby preventing loop 94 from being withdrawn from eyelet 90. Tether 92 can be used to pull device 80 proximally or to hold device 80 stationary against a distal force exerted on device 80, such as during recapture. Tether 92 may also be used to hold device 80 tightly against pusher 82 during delivery and deployment of the device.

To release device 80 from the delivery mechanism, hitch wire 96 may be disengaged from device 80. In this embodiment, hitch wire 96 is disengaged by moving the hitch wire proximally through the action of a hitch wire actuator 98 while holding device 80 stationary with pusher 92. When hitch wire 96 is disengaged from device 80 and moved proximal to the loop of tether 92, proximal movement of tether 92 will pull the tether's loop out of eyelet 90.

Figure 10:
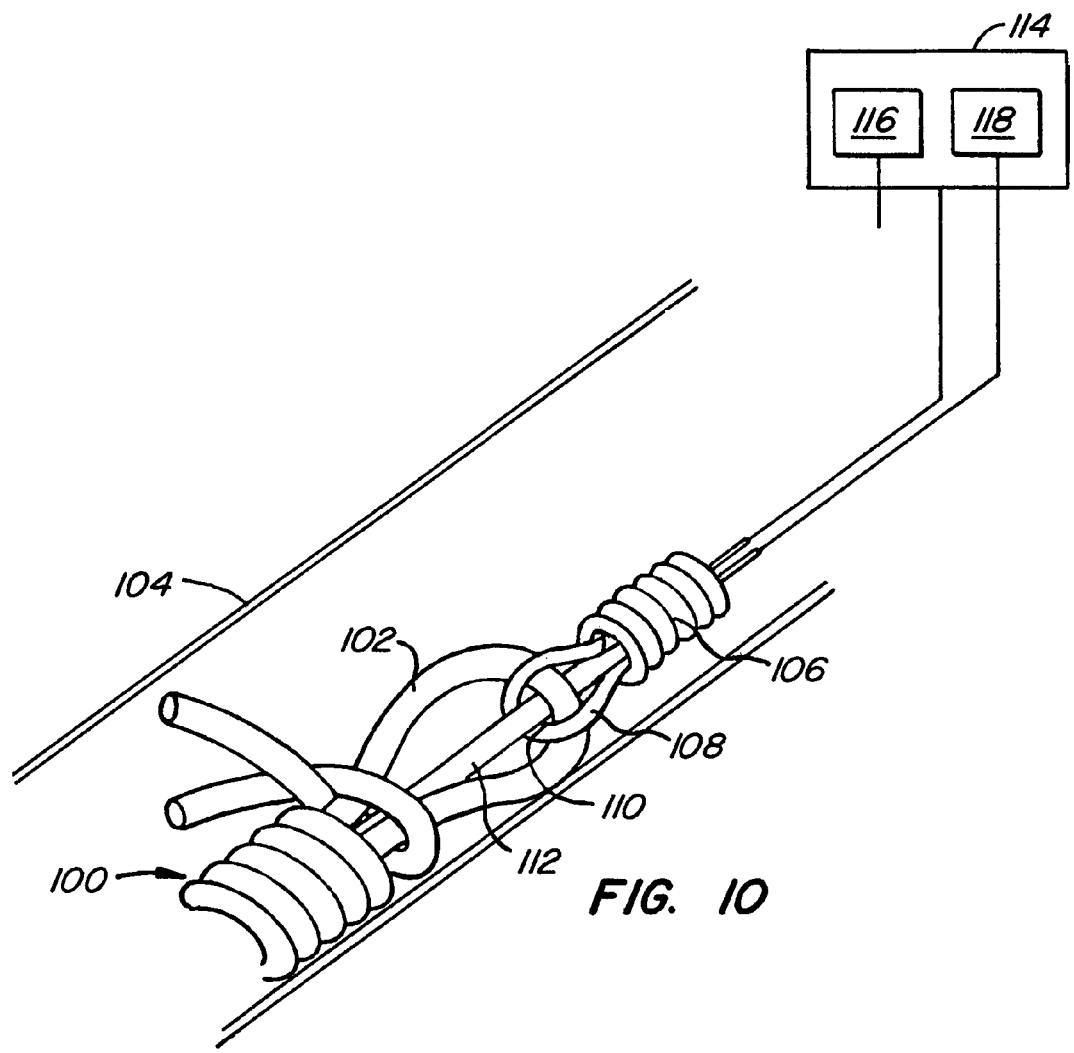
FIG. 10 shows another attachment mechanism for a tissue shaping device delivery system.

FIG. 10 shows another attachment mechanism for a tissue shaping device and its delivery mechanism. As in the embodiment of FIG. 9, an eyelet 102 extends proximally from tissue shaping device 100 within delivery catheter 104. The distal end of pusher 106 has an eyelet 108 at its distal end that overlaps with device eyelet 102 to form an overlap opening 110. A hitch wire 112 extends through pusher 106 and overlap opening 110 into the proximal end of tissue shaping device 100.

As in the previous embodiment, catheter 104, pusher 106 and hitch wire 112 extend out of the patient to a handle or other housing 114. Pusher 106 may be operated by an actuator or by handle 114 to advance device 100 distally through catheter 104 or to hold device 100 stationary against a proximal force exerted on device 100, such as when delivery catheter 104 is withdrawn proximally by an actuator 116 supported by handle 114. Also, because the attachment mechanism of this embodiment holds pusher 106 against device 100, pusher 106 can be used to pull device 100 proximally or to hold device 100 stationary against a distal force exerted on device 100, such as during recapture.

To release device 100 from the delivery mechanism, hitch wire 112 may be disengaged from device 100. As in the embodiment of FIG. 9, hitch wire 112 is disengaged by moving the hitch wire proximally through the action of a hitch wire actuator 118 while holding device 100 stationary with pusher 106. When hitch wire 112 is disengaged from device 100 and moved proximal to the overlap opening 110, device 100 is disengaged from the delivery mechanism.

Figure 11:
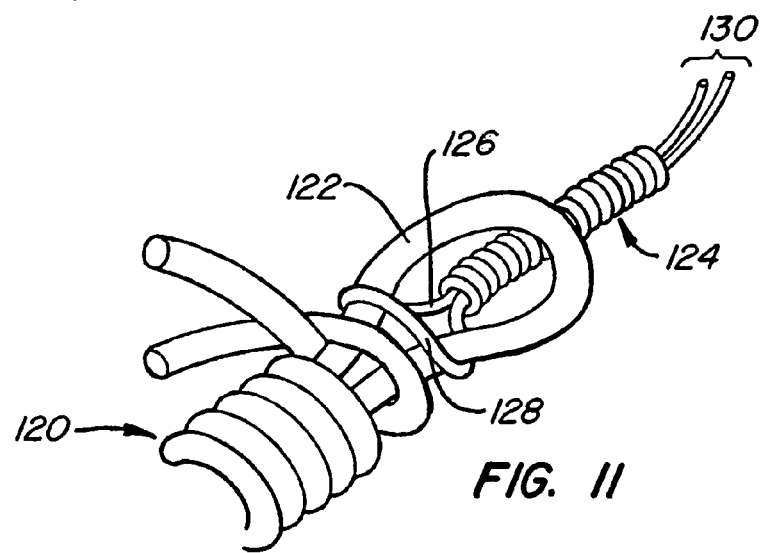
FIG. 11 shows yet another attachment mechanism for a tissue shaping device delivery system.

FIG. 11 shows an attachment mechanism that can be used to engage a tissue shaping device after initial deployment for possible recapture of the device. As in other embodiments, device 120 has a proximal eyelet 122. Retractor 124 has a cable 126 extending through it. Cable 126 has a loop 128 at its distal end and free ends 130 extending out of the patient, possibly to a handle or housing (not shown). To engage device 120, retractor 124 and looped cable 126 are advanced to device 120 with loop 128 arranged to be large enough to surround eyelet 122. When loop 128 passes over and around eyelet 122, one or both of the free ends of cable 126 are pulled proximally to pull loop 128 tightly about eyelet 122, as shown. Retractor 124 may then be used to pull device 120 proximally, such as for recapture into a catheter. Alternatively, retractor may be used as a pusher to apply a distally directed force on device 120, if needed.

Figure 12:
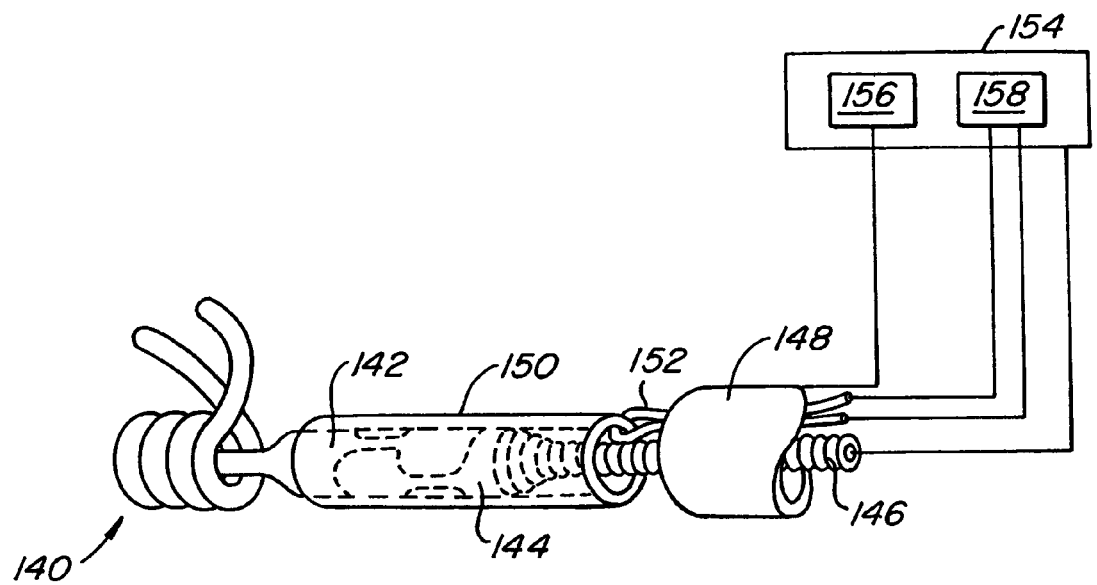
FIG. 12 shows still another attachment mechanism for a tissue shaping device delivery system.
Figure 13:
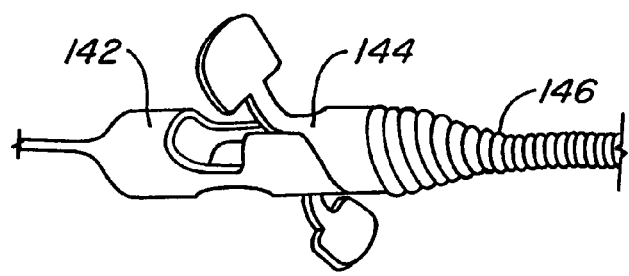
FIG. 13 is a detail of the attachment mechanism of FIG. 12 in a disengaged configuration.

FIGS. 12 and 13 show yet another attachment mechanism between a tissue shaping device and a delivery mechanism. Tissue shaping device 140 has a locking structure 142 at its proximal end designed to mate with a corresponding locking structure 144 at the distal end of a pusher 146 within catheter 148. A cover 150 is disposed over the interlocked locking structures to maintain the connection between device 140 and pusher 146. A tether 152 is connected to cover 150.

Catheter 148, pusher 146 and tether 152 extend out of the patient to a handle or other housing 154. Pusher 146 may be operated by an actuator or by handle 154 to advance device 140 distally through catheter 148 or to hold device 140 stationary against a proximal force exerted on device 140, such as when delivery catheter 148 is withdrawn proximally by an actuator 156 supported by handle 154. Also, because the attachment mechanism of this embodiment holds pusher 146 against device 140, pusher 146 can be used to pull device 140 proximally or to hold device 140 stationary against a distal force exerted on device 140, such as during recapture.

To release device 140 from the delivery mechanism, tether 152 may be pulled proximally to pull cover 150 off of the locking structures 142 and 144, such as by use of an actuator 158, while holding device 100 stationary with pusher 146. Locking structures 142 and 144 are preferably formed from a shape memory material. When cover 150 is removed from the locking structures, the locking structures assume an unstressed configuration such as that shown in FIG. 13, thereby disengaging device 140 from pusher 146.

Figure 14:
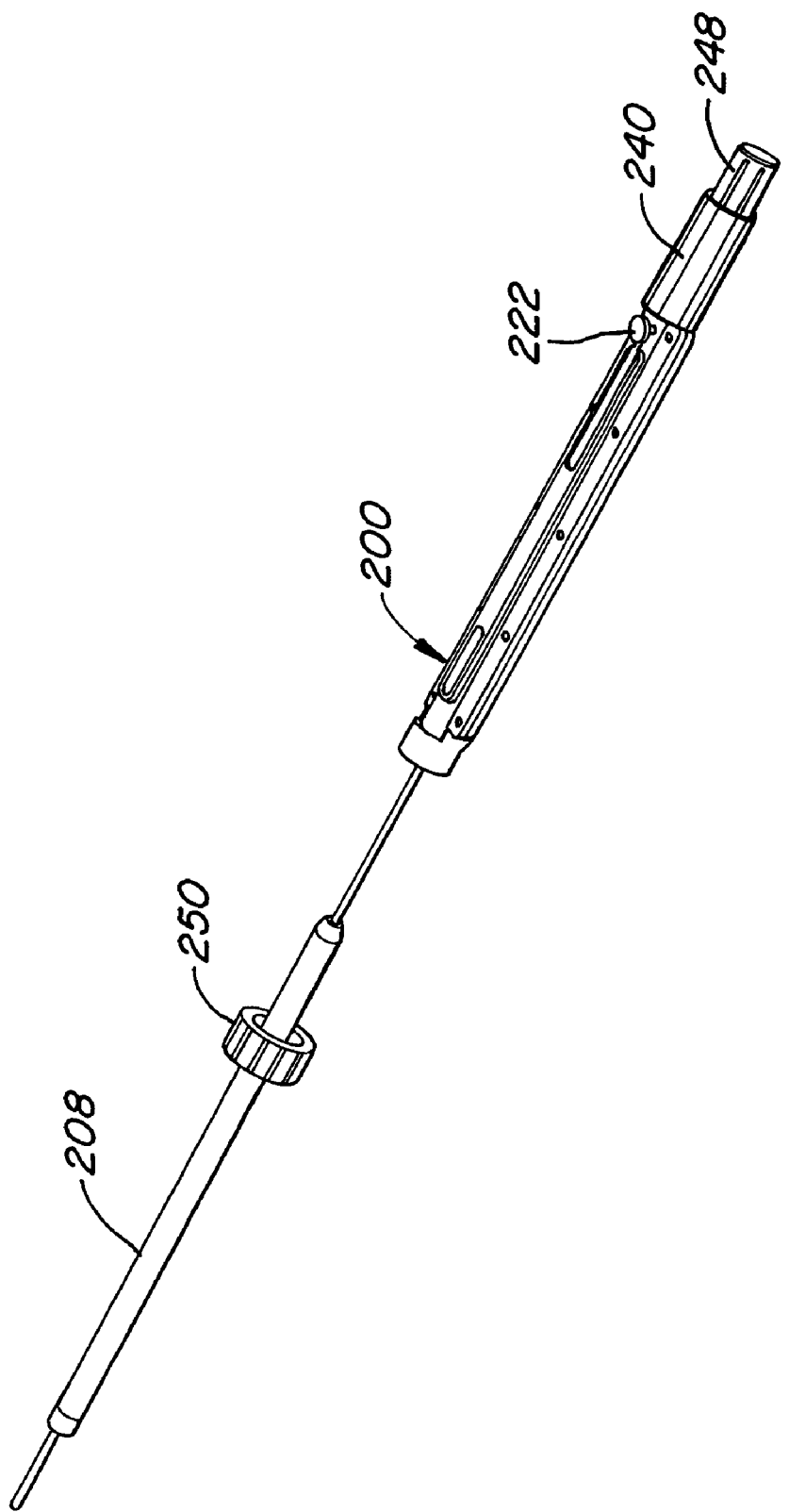
FIG. 14 is a perspective view of a tissue shaping device delivery system according to this invention.

FIGS. 14-21 show a tissue shaping device delivery and deployment system according to one embodiment of this invention. The system includes a handle 200 supporting delivery, deployment and attachment mechanisms for a tissue shaping device 202 having distal and proximal expandable anchors 204 and 206, respectively. In FIG. 14, the device is disposed in a compressed configuration within a cartridge 208. In this embodiment, the device will go directly from cartridge 208 into a delivery catheter for delivery and deployment in a patient.

Figure 15:
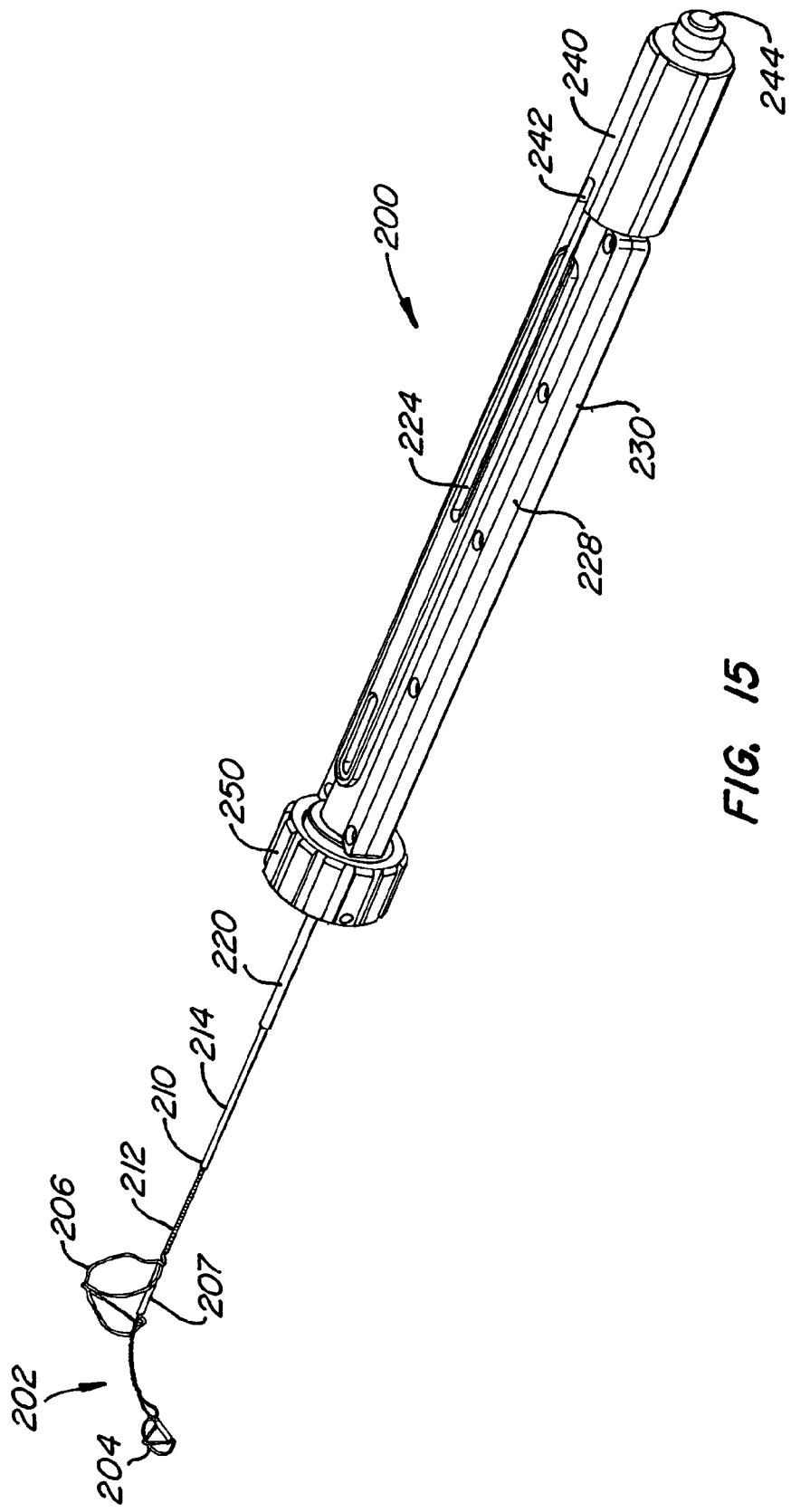
FIG. 15 is another perspective view of the tissue shaping device delivery system of FIG. 14 showing a tissue shaping device without a cartridge.

As shown in FIG. 15, a pusher 210 abuts the proximal end of tissue shaping device 202. Pusher 210 should be flexible and incompressible, and its properties may vary from section to section along its length. In one embodiment, pusher 210 is formed at its distal end from a coiled spring 212 (e.g., to facilitate bending) and thereafter from a stainless steel hypotube 214. Device 202 is attached to pusher 210 via a tether 216 and hitch wire 218 in an arrangement such as that described above with respect to FIG. 9. The tether has to be strong enough to apply an appropriate proximally directed force during delivery, deployment and recapture; the hitch wire has to be stiff enough not to kink or pull through the eyelet when the tether is pulled proximally. For example, for use in a tissue shaping system intended to treat mitral valve regurgitation via the coronary sinus, the tether preferably can pull up to 18 pounds. In one embodiment, tether 216 is formed from 0.07 inch stainless steel with a full hard temper, and hitch wire is formed from 0.11 inch 304 stainless steel. Tether 216 and hitch wire 218 extend through the pusher's lumen. Pusher 210, tether 216 and hitch wire 218 are attached to and supported by handle 200, as discussed below with respect to FIGS. 17 and 18.

Figure 16:
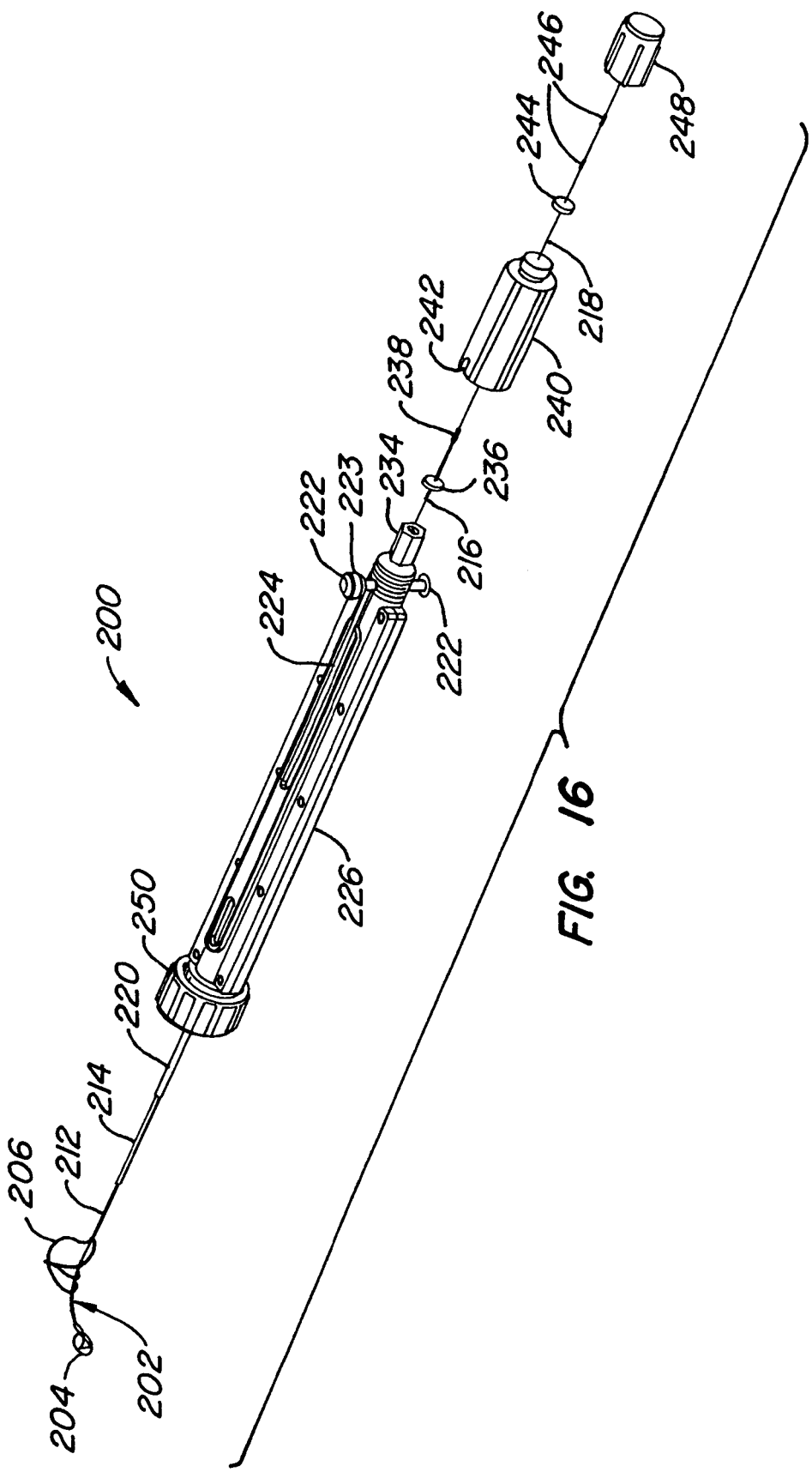
FIG. 16 is an exploded view of the tissue shaping device and delivery system of FIG. 15.
Figure 17:
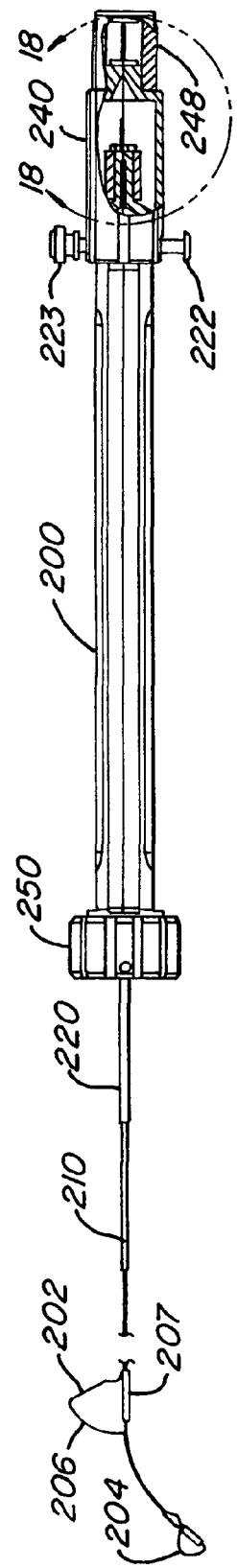
FIG. 17 is a partial cross-sectional view of certain portions of the tissue shaping device delivery system of FIG. 15.

Surrounding pusher 210 is a locking sleeve 220 whose inner diameter is close to the outer diameter of pusher 210 in order to minimize backflow of blood or other fluids. The proximal end of locking sleeve 220 is supported by a slider (not shown) resting in a circular track formed by the handle housing. Actuator knobs 222 are threaded into holes formed in the sides of the slider, and the slider and actuator knobs are attached to the locking sleeve 220 by adhesive. One of the actuator knobs may be provided with an actuation interlock, such as a screw down portion 223 that screws against the handle housing to prevent movement of the actuator knobs and locking sleeve. As shown in FIG. 16, actuator knobs 222 fit in tracks 224 formed in handle 200.

Figure 18:
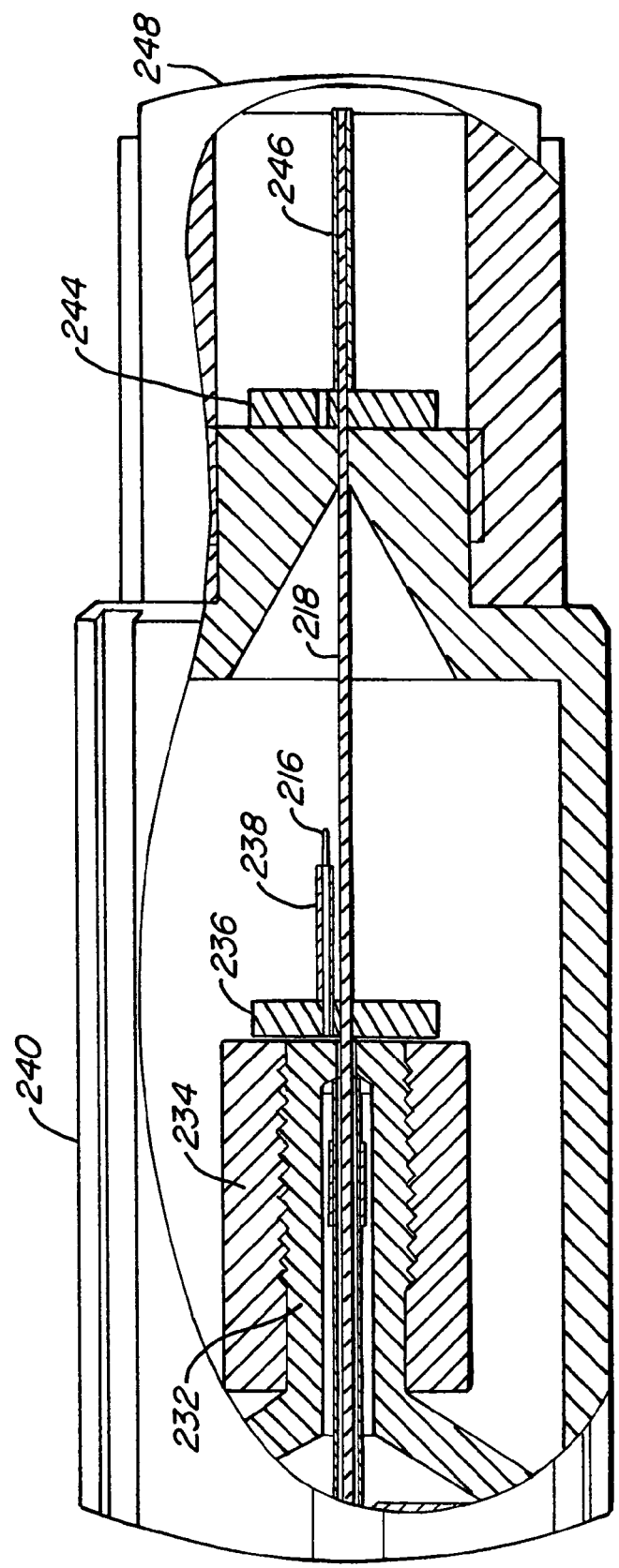
FIG. 18 is a detailed cross-sectional view of a portion of the tissue shaping device shown in FIG. 17.

When assembling the delivery system, pusher 210 is placed within locking sleeve 220. Handle housing 226 has two parts, 228 and 230, which are placed and screwed together around the locking sleeve and pusher. As shown in FIG. 18, assembly of the two halves of handle housing 226 attaches the proximal end of pusher 210 to handle 200 with a press fit connection (which may be supplemented with adhesive) in a pusher connection area 232 of handle housing 226. Locking sleeve actuator knobs 222 are in the tracks 224, as discussed above.

Hitch wire 218 and tether 216 are then threaded into the central lumen of pusher 210, and device 202 is attached by placing the looped end of tether 216 through an eyelet (not shown) on the proximal end of device 202. Hitch wire 218 passes through the looped end of tether 216 into the device's proximal anchor crimp tube 207. (Placement of the distal end of the hitch wire inside the crimp tube helps prevent injury to the patient's heart or blood vessels by the hitch wire.)

Tether 216 and hitch wire 218 extend proximally from the proximal end of pusher 210 through the proximal end of pusher connection area 232 and through holes formed in a disc 236 disposed proximal to pusher connection area 232 and jack nut 234. A crimp tube 238 or other connector attaches to the proximal end of tether 216 to prevent it from passing distally through disc 236; excess portions of tether 216 may be cut off. A jack nut 234 threaded around the outside of pusher connection area 232 may then be rotated about pusher connection area 232 to move jack nut 234, disc 236 and crimp tube 238 proximally with respect to the handle housing, thereby tightening tether 216 and pulling device 202 tight against pusher 210.

A release knob 240 is threaded onto handle housing 226 around pusher connection area 232 with track portions 242 lining up with handle tracks 224, as shown. Hitch wire 218 extends proximally through release knob 240 and a second disc 244, and the proximal end of hitch wire 218 is crimped with one or more crimp tubes 246 to prevent distal movement of hitch wire 218 with respect to the handle. A cap 248 covers the distal end of hitch wire 218 to prevent injury to the user from the sharp wire end.

Prior to delivery and deployment, the eyelet of the proximal anchor 206 is pulled proximally over the pusher coil 212, and the eyelet of the distal anchor is pulled proximally over the connector between the two anchors. Device 202 is then compressed and loaded into cartridge 208 with the distal anchor 204 at the distal end of the cartridge and with the pusher, tether and hitch wire extending from the proximal end of cartridge 208 into handle 200. A loading tool, such as a two-piece funnel, may be used to assist in the compression and loading of the device into the cartridge. In a preferred embodiment, a control nut 250 is threaded onto the threaded exterior of cartridge 208, as shown in FIG. 14.

Figure 19:
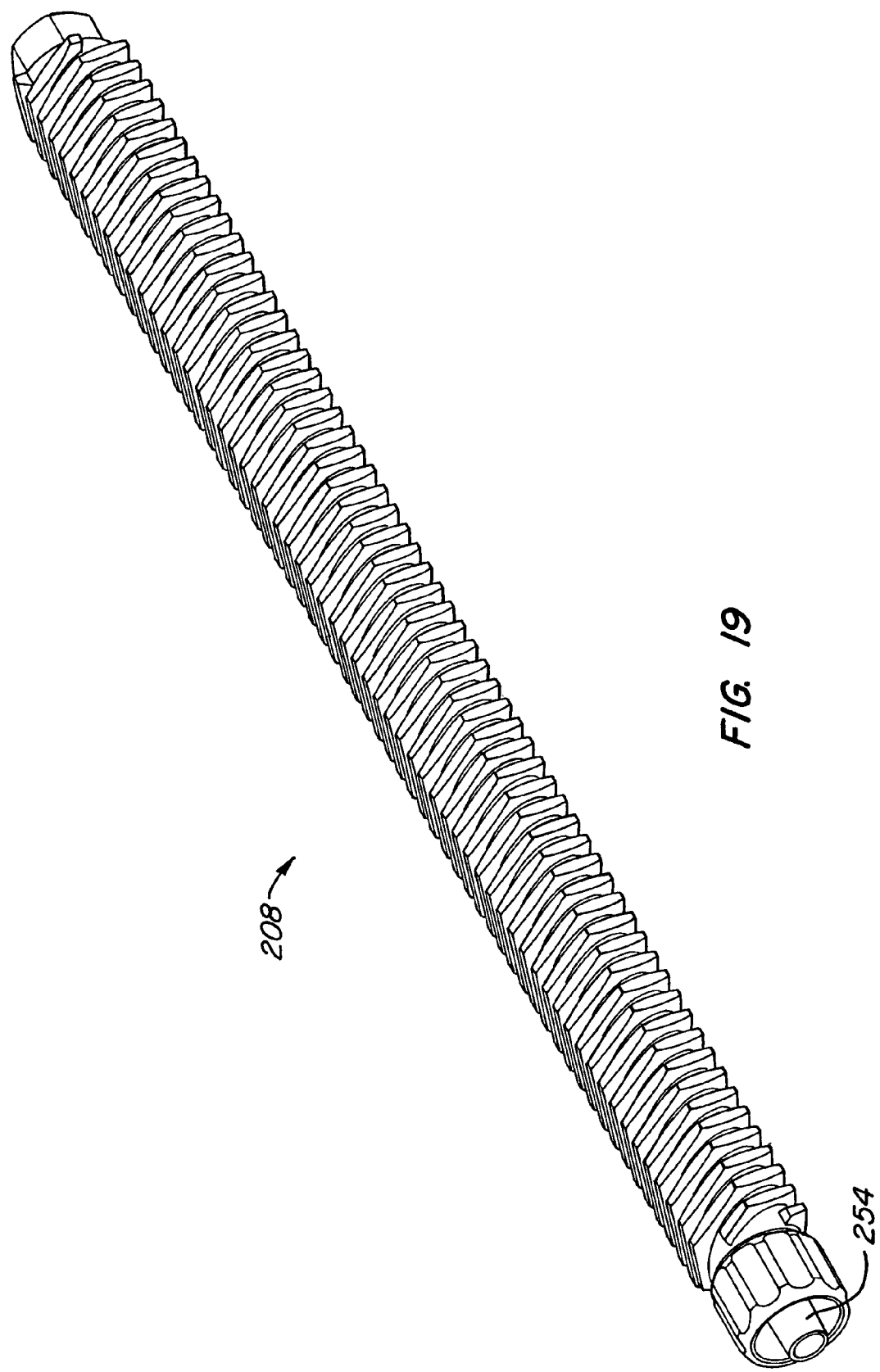
FIG. 19 is a perspective view of a cartridge for the tissue shaping device delivery system of FIG. 14.
Figure 20:
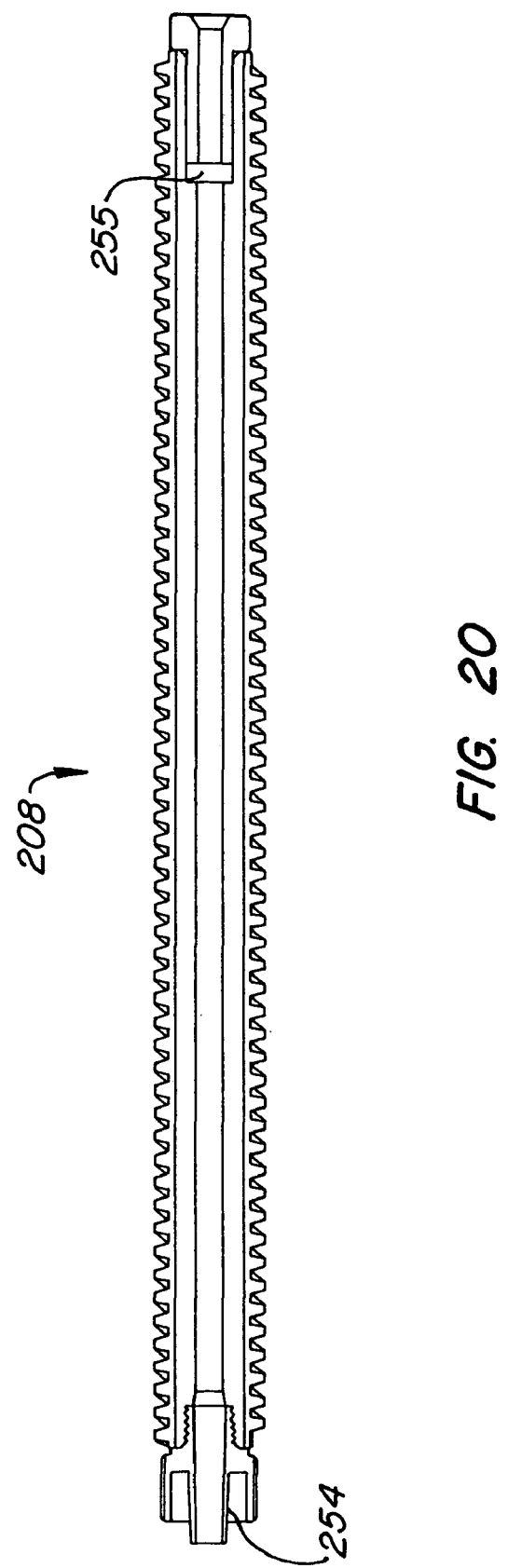
FIG. 20 is a cross-sectional view of the cartridge of FIG. 19.

Cartridge 208 is shown in more detail in FIGS. 19 and 20. Cartridge 208 has a central lumen 252 with a lubricious polymeric liner. The diameter of central lumen 252 may be substantially the same as the diameter of a delivery catheter to be used to deliver device 202. Alternatively, the diameter of central lumen 252 may be larger than the intended delivery catheter diameter to minimize stress on the tissue shaping device during sterilization, temperature changes during shipping, etc. Cartridge 208 has a male luer connector 254 at its distal end for mating with a corresponding female luer connector on the delivery catheter, as described below. The outside of the cartridge preferably has at least one flat side in order to prevent rotation of the cartridge with respect to the handle during deployment, as described below. In the embodiment shown in FIGS. 19 and 20, cartridge 208 has a hexagonal cross-section presenting six possible orientations for mating with a flat side formed on the inside of the handle during delivery and deployment of the tissue shaping device. An O-ring seal 255 at the proximal end of cartridge 208 seals around locking sleeve 220 to prevent backflow of blood or other fluids while still permitting relative movement between locking sleeve 220 and cartridge 208.

Figure 21:
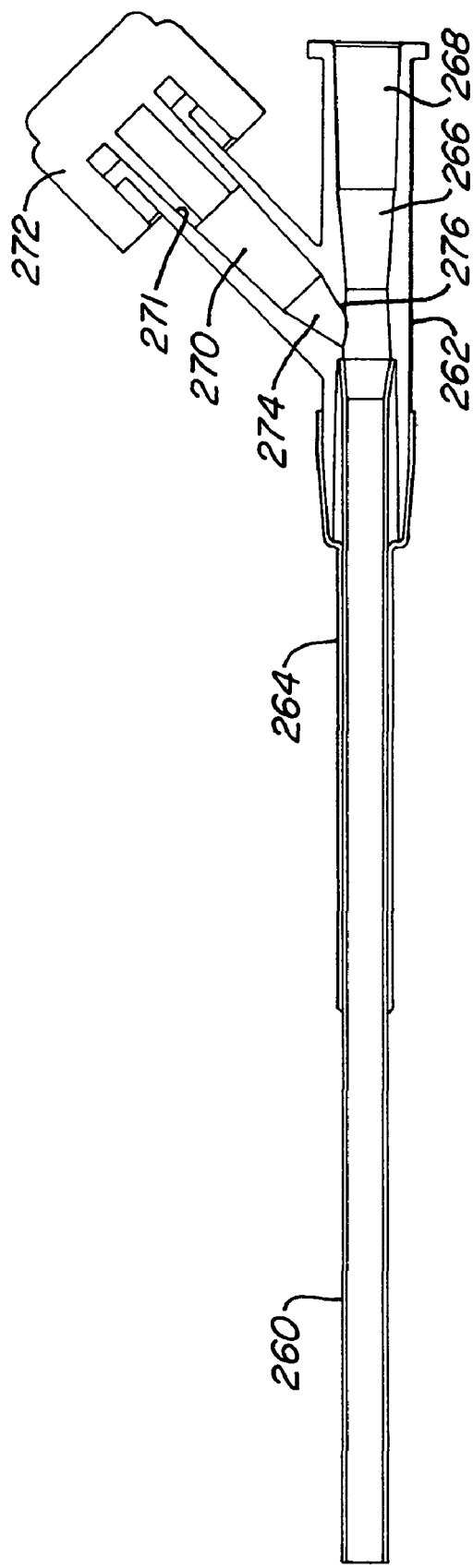
FIG. 21 is a cross-sectional view of a delivery catheter and connector for use with the tissue shaping device delivery system of FIGS. 14-20.

FIG. 21 shows a delivery catheter 260 and connector 262 for use with the cartridge and handle of this invention. The length and diameter of catheter 260 depends on the application. For example, to deliver a tissue shaping device to the coronary sinus through the jugular vein to treat mitral valve regurgitation, catheter 260 may be a nine french diameter catheter at least 65 cm. long. Catheter 260 may also have a radiopaque market on its distal end for visualization via fluoroscopy. When it needs to negotiate bends and turns to reach the target treatment site, catheter 260 may be more flexible at its distal tip than along its proximal end. Catheter 260 may also be braided to increase its compression strength, which aids in locking anchors, recapturing devices, etc., as described below.

Y-shaped connector 262 is attached to the proximal end of catheter 260 by adhesive and a shrink tube 264. Connector 262 has a main channel 266 with a female luer connection 268 adapted to mate with the luer connection of cartridge 208. A second channel 270 meets the main channel 266 proximal to the proximal end of delivery catheter 260. Second channel 270 also has a luer connection to permit it to be connected to a source of imaging contrast agent, such as dye. Second channel 270 enables a dye source to be connected and for dye to be injected even during use of the main channel to deliver and deploy the tissue shaping device. (The space between the inner diameter of the delivery catheter and the outer diameter of the locking sleeve permits contrast dye to flow distally to the target treatment site.) A cap 272 may be used to close off second channel 270 when not in use. The diameters of both channels transition down from the standard luer fitting size to the diameter of the delivery catheter.

A first step for using the tissue shaping system of this invention to treat mitral valve regurgitation is to access the coronary sinus of the patient's heart. One way of reaching the coronary sinus is to insert a sheath into the patient's jugular vein. A guide catheter with a precurved tip may then be inserted into the sheath and advanced to coronary sinus ostium within the right atrium of the heart. A guidewire may then be advanced through the guide catheter and into the coronary sinus, and the guide catheter may be removed from the patient, leaving the guidewire behind. The delivery catheter 260 may then be advanced along the guidewire, and the guidewire may be removed.

The anatomy of the heart varies from patient to patient. For example, the diameter and length of the coronary sinus are patient-dependent as well as the location of coronaries arteries that may pass between the coronary sinus and the heart. One optional method step, therefore, is to introduce dye or another imaging contrast agent into the coronary sinus through the delivery catheter (such as through the Y-shaped connector 262) to perform a venogram while performing an angiogram on the coronary arteries in a known manner. These images will identify the relative positions of the coronary sinus and coronary arteries and will give a relative indication of the length and diameter of the coronary sinus at the target treatment site.

In addition, in order to calibrate the venogram with the actual size of the imaged vessels, a marker catheter may be inserted into the coronary sinus through the delivery catheter during the venogram. The marker catheter has radiopaque markings a fixed distance apart. By measuring on the venogram the distance between markings on the marker catheter, a correction factor may be devised to correct the measured diameter and length of the coronary sinus. Alternatively, radiopaque markings may be added to the delivery catheter itself, thereby eliminating the need to insert a marker catheter to obtain the correction factor measurements. Dye may also be injected during delivery and deployment of the tissue shaping device for imaging purposes.

After removal of the marker catheter, the delivery system may be attached to the delivery catheter. Prior to the start of the procedure, locking sleeve 220 is in its proximal-most position so that locking sleeve actuator knobs 222 are in slots 242 of release knob 240, and screw down portion 223 is screwed against housing 226 to hold locking sleeve 220 in place. Pusher 210 and locking sleeve 220 extend from the distal end of handle 200 to the device 202 within cartridge 208. The lengths of pusher 210 and locking sleeve 220 correspond to the length of delivery catheter 260, as discussed below. Lengths of pusher 210 and locking sleeve 220 may be exposed between handle 200 and cartridge 208.

To begin delivering tissue shaping device 202 to the patient's coronary sinus, cartridge 208 (containing tissue shaping device 202) and delivery catheter 260 are then connected at luer connection 268 of the main channel of Y-connector 262. The distal tip of the delivery catheter is in place in the coronary sinus at the distal end of the target treatment site. To begin delivery of the device from cartridge 208 into delivery catheter 260, handle 200 is advanced distally toward cartridge 208 and delivery catheter 260. As the handle advances toward the cartridge and toward the patient, pusher 210 moves device 202 distally out of cartridge 208 into Y-connector 262 and then into delivery catheter 260. The structure of the point where the Y-connector's second channel 270 meets the main channel 266—specifically, reduced diameter portion 274 and tab 276—helps prevent the tissue shaping device from expanding and getting caught at the junction of the two channels.

In certain embodiments of the invention, the advancing handle 200 reaches cartridge 208 when or before device 202 reaches the distal end of delivery catheter 260. For example, in the embodiment shown in FIGS. 14-21, the relative lengths of device 202, pusher 210, handle 200 and delivery catheter 260 are such that the distal end of handle 200 reaches the proximal end of cartridge 208 before device 202 reaches the distal end of delivery catheter 260. After this point, further advancement of handle 200 places handle housing 226 around cartridge 208 so that cartridge 208 moves inside the handle. A flat interior surface (not shown) formed in handle 200 mates with one of the flat sides of cartridge 208 to prevent relative rotation between the cartridge and the handle as control nut 250 rotates.

In one embodiment, rotating control nut 250 is threaded onto cartridge 208 prior to use of the system to treat a patient, as shown in FIG. 14. The location of control nut 250 on cartridge 208 depends on the length of the device 202 within cartridge 208 as well as the relative lengths of the pusher and delivery catheter. In this embodiment, these elements are sized and configured so that control nut 250 engages with, and snaps to, the distal end of handle 200 at the point during device delivery when device 202 has reached the distal end of delivery catheter 260. This action engages cartridge 208 with handle 200 for controlled delivery and deployment of tissue shaping device 202. Alternatively, control nut 250 can be disposed on the distal end of handle 200 from the start. In this case, cartridge 208 engages handle 200 through control nut 250 as soon the proximal end of cartridge 208 reaches handle 200, which may be before device 202 has reached the distal end of delivery catheter 260.

After cartridge 208 engages handle 200 through control nut 250, all further relative movement between cartridge 208 and handle 200 is controlled by rotating control nut 208. When tissue shaping device 202 is at the distal end of catheter 260 at the distal end of the target treatment site (as determined fluoroscopically, e.g.) the physician ceases moving handle 200 toward the patient. Instead, handle 200 (and therefore device 202) is held stationary while cartridge 208 and delivery catheter 260 are pulled proximally by rotating control nut 250. This action exposes the device's distal anchor 204, which begins to self-expand. Control nut 250 is then rotated the other direction to advance delivery catheter 260 distally to apply a force to the proximal side of anchor 204 to further expand and lock the anchor, i.e., by advancing the anchor's lock loop over its lock bump, as described above. Thus, control nut 250 acts as an actuator for expanding and locking the device's distal anchor.

After locking the distal anchor, a proximal cinching force is applied to the device through tether 216 to reshape the mitral valve annulus by moving handle 200 proximally away from the patient, preferably while observing the status of the patient's mitral valve regurgitation and vital signs, such as described in U.S. patent application Ser. No. 10/366,585, "Method of Implanting a Mitral Valve Therapy Device." Contrast dye may be injected via connector 262 to visualize the anchor while cinching. When an appropriate amount of mitral valve regurgitation has been achieved, control nut 250 is rotated while holding handle 200 in place to pull delivery catheter 260 proximally with respect to tissue shaping device 202, thereby exposing proximal anchor 206, which begins to self-expand.

In one embodiment of the invention, locking sleeve 220 is used in place of the larger diameter delivery catheter to further expand and lock proximal anchor 206 in order to avoid inadvertent recapture of the proximal anchor by the delivery catheter. Screw down portion 223 of knobs 222 is loosened to permit knobs 222 to slide forward in tracks 224, thereby advancing locking sleeve 220 distally toward anchor 206. Locking sleeve 220 applies a distally directed force on the proximal side of anchor 206 to further expand and lock the anchor, i.e., by advancing the anchor's lock loop over its lock bump, as described above. Thus, knobs 222 act as an actuator for expanding and locking the device's proximal anchor. Expansion and locking of the proximal anchor maintains the cinching action and, therefore, the reduction in mitral valve regurgitation caused by the device's reshaping of the mitral valve annulus.

Alternatively, the delivery catheter can be used to expand and lock the proximal anchor in the same manner as the distal anchor.

The delivery system of this embodiment enables the tissue shaping device to be fully deployed before it is detached from the delivery system. If the tissue shaping device's placement is satisfactory, the device is unhitched from the delivery system. To unhitch, release knob 240 is rotated to move release knob and the attached hitch wire 218 proximally with respect to device 202. This action pulls the distal end of hitch wire 218 out of the device's proximal anchor crimp 207 and releases the looped end of tether 216, thereby disengaging device 202 from the delivery system. The delivery catheter, tether and hitch wire may then be removed from the patient.

The slots 242 in release knob 240 prevent rotation of release knob 240 when locking sleeve 220 is in its proximal-most position. This device release interlock feature helps ensure that the locking sleeve has been used to lock the proximal anchor before the tissue shaping device is disengaged from the delivery system.

In certain instances, after initial deployment but before disengaging the hitch wire and tether the tissue shaping device may need to be recaptured and either removed from the patient or deployed at a different site. In that case, locking sleeve 220 is advanced distally to the proximal side of proximal anchor 206 by moving knobs 222 forward in tracks 224. While holding handle 200 stationary to hold device 202 against distal movement through the action of tether 216, control nut 250 is rotated to advance delivery catheter 260 distally over locking sleeve 220 to and over proximal anchor 206, deforming anchor 206 so that it fits back inside catheter 260. In this manner, control nut 250 is used as a recapture actuator; use of the control nut to apply the recapture force helps prevent a sudden inadvertent distal advancement of the catheter when the anchor collapses and enters the catheter. Once the proximal anchor has been recaptured into the delivery catheter, the catheter is then advanced further distally to recapture distal anchor 204 in the same way. Device 202 can then be moved or removed from the patient.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A method of delivering and deploying a tissue shaping device in a coronary sinus within a patient, the tissue shaping device comprising an anchor, the method comprising:
   inserting a delivery catheter into the coronary sinus;
   percutaneously delivering the device to a target site within the coronary sinus through the delivery catheter;
   operating an actuator in a first direction to allow the anchor to self-expand outside of the delivery catheter; and
   operating the actuator in a second direction to lock the anchor,
   wherein operating the actuator to lock the anchor occurs after operating the actuator to allow the anchor to self-expand outside of the delivery catheter, and
   wherein the second direction is opposite the first direction.

2. The method of claim 1 wherein the step of operating the actuator to allow the anchor to self-expand comprises operating the actuator to move the delivery catheter proximally.

3. The method of claim 1 wherein the step of operating the actuator to lock the anchor comprises engaging the anchor with an actuation force.

4. The method of claim 3 wherein the step of engaging the anchor with an actuation force comprises expanding and locking the anchor.

5. The method of claim 1 wherein the anchor is a first anchor, the tissue shaping device further comprising a second anchor, the method further comprising operating the actuator to expose the second anchor.

6. The method of claim 5 further comprising permitting the second anchor to self-expand after exposing the second anchor.

7. The method of claim 5 further comprising expanding and locking the second anchor.

8. The method of claim 1 further comprising delivering an imaging contrast agent through the delivery catheter to the treatment site while the tissue treatment device is within the lumen.

9. The method of claim 1 further comprising releasing the tissue shaping device from a delivery mechanism.

10. The method of claim 1 further comprising recapturing the tissue shaping device into the delivery catheter.

11. The method of claim 1 wherein the percutaneously delivering step comprises moving the tissue shaping device from a cartridge into the delivery catheter.

12. The method of claim 11 further comprising attaching the cartridge to the delivery catheter.

13. The method of claim 12 wherein the attaching step comprises attaching the cartridge to a connector extending from the delivery catheter.

14. A method of delivering and deploying a tissue shaping device in a coronary sinus within a patient, the tissue shaping device comprising an anchor, the method comprising:
inserting a delivery catheter into the coronary sinus;
percutaneously delivering the device to a target site within the coronary sinus through the delivery catheter;
operating an actuator to move the delivery catheter proximally to expose the anchor; and
operating the actuator to move the delivery catheter distally to lock the anchor.

15. A method of delivering and deploying a tissue shaping device in a lumen within a patient, the tissue shaping device comprising an anchor, the method comprising:
inserting a delivery catheter into the lumen;
percutaneously delivering the device to a target site within the lumen through the delivery catheter;
operating a first actuator to expose the anchor; and
operating the first actuator to lock the anchor,
wherein the anchor is a first anchor, the tissue shaping device further comprising a second anchor disposed proximally to the first anchor, the method further comprising operating the first actuator to expose the second anchor; and
operating a second actuator to expand and lock the second anchor.

16. A method of delivering and deploying a tissue shaping device in a lumen within a patient, the tissue shaping device comprising an anchor, the method comprising:
inserting a delivery catheter into the lumen;
percutaneously delivering the device to a target site within the lumen through the delivery catheter;
operating a first actuator to expose the anchor;
operating the first actuator to lock the anchor;
operating a second actuator to release the tissue shaping device from a delivery mechanism.

17. A method of delivering and deploying a tissue shaping device in a lumen within a patient, the tissue shaping device comprising an anchor, the method comprising:
inserting a delivery catheter into the lumen;
percutaneously delivering the device to a target site within the lumen through the delivery catheter;
operating an actuator to expose the anchor;
operating the actuator to lock the anchor; and
releasing the tissue shaping device from a delivery mechanism by disconnecting a tether from the tissue shaping device.

18. The method of claim 17 wherein the disconnecting step comprises removing a hitch wire from the tissue shaping device.

19. A method of delivering and deploying a tissue shaping device in a lumen of a patient, the tissue shaping device comprising an anchor, the method comprising:
inserting a delivery catheter into the lumen;
moving the device from a cartridge into the delivery catheter;
delivering the device to a target site within the lumen, comprising moving a pusher distally to push the device through the delivery catheter, wherein the pusher is attached to a handle, the delivering step further comprising moving the handle toward the cartridge;
engaging the cartridge with the handle;
operating an actuator to move the delivery catheter with respect to the anchor to expose the anchor, wherein the actuating step comprises rotating the actuator after the engaging step; and
expanding the anchor.

20. A method of delivering and deploying a tissue shaping device in a lumen of a patient, the tissue shaping device comprising a distal anchor and a proximal anchor, the method comprising:
inserting a delivery catheter into the lumen;
moving the device from a cartridge into the delivery catheter;
delivering the device to a target site within the lumen;
operating a first actuator to move the delivery catheter with respect to the distal anchor to expose the distal anchor;
expanding the distal anchor;
operating the first actuator to move the delivery catheter proximally to expose the proximal anchor;
expanding the proximal anchor; and
locking the proximal anchor in the expanded configuration, wherein locking the proximal anchor comprises applying an external actuation force on the proximal anchor, and wherein
the step of applying an external actuation force on the proximal anchor comprises operating a second actuator to move a proximal anchor locking device distally.

21. A method of delivering and deploying a tissue shaping device in a lumen within a patient, the tissue shaping device comprising an anchor, the method comprising:
inserting a delivery catheter into the lumen;
percutaneously delivering the device to a target site within the lumen through the delivery catheter;
operating an actuator to expose the anchor completely outside of the delivery catheter; then
operating the actuator to lock the anchor.

22. The method of claim 21 further comprising expanding the anchor outside of the delivery catheter.

23. The method of claim 21 wherein operating the actuator to expose the anchor comprises moving the delivery catheter proximally to expose the anchor.

24. The method of claim 23 wherein operating the actuator to lock the anchor comprises moving the delivery catheter distally to lock the anchor.

25. A method of delivering and deploying a tissue shaping device in a lumen of a patient, the tissue shaping device comprising an anchor, the method comprising:
inserting a delivery catheter into the lumen;
moving the device from a cartridge into the delivery catheter;
delivering the device to a target site within the lumen;
engaging a handle with the cartridge;
operating an actuator to move the delivery catheter with respect to the anchor to expose the anchor; and
expanding the anchor.

26. The method of claim 25 further comprising loading the tissue shaping device into the cartridge.

27. The method of claim 25 wherein the delivering step comprises moving a pusher distally to push the device through the delivery catheter.

28. The method of claim 27 wherein the pusher is attached to the handle, the delivering step comprising moving the handle toward the cartridge.

29. The method of claim 25 further comprising moving the cartridge at least partially into the handle after the engaging step.

30. The method of claim 25 wherein the engaging step comprises mating the actuator with the cartridge.

31. The method of claim 25 wherein the actuator is mounted on the cartridge prior to the engaging step, the engaging step comprising attaching the actuator to the handle.

32. The method of claim 25 wherein the delivering step comprises delivering the device substantially to a distal end of the delivery catheter when the cartridge engages the handle.

33. The method of claim 25 wherein the expanding step comprises permitting the anchor to self-expand.

34. The method of claim 25 further comprising locking the anchor in an expanded configuration.

35. The method of claim 34 wherein the locking step comprises applying an external actuation force on the anchor.

36. The method of claim 35 wherein the applying step comprises operating the actuator to move the delivery catheter distally.

37. The method of claim 25 wherein the expanding step comprises applying an external actuation force on the anchor.

38. The method of claim 37 wherein the applying step comprises operating the actuator to move the delivery catheter distally.

39. The method of claim 25 further comprising applying a proximally directed force on the device after the expanding step.

40. The method of claim 39 wherein the applying step comprises pulling proximally on a tether attached to the device.

41. The method of claim 39 wherein the anchor comprises a distal anchor, the method further comprising operating the actuator to move the delivery catheter proximally to expose a proximal anchor after the applying step.

42. The method of claim 25 wherein the anchor comprises a distal anchor, the method further comprising operating the actuator to move the delivery catheter proximally to expose a proximal anchor.

43. The method of claim 42 further comprising expanding the proximal anchor.

44. The method of claim 43 further comprising locking the proximal anchor in an expanded configuration.

45. The method of claim 44 wherein the step of locking the proximal anchor comprises applying an external actuation force on the proximal anchor.

46. The method of claim 45 wherein the step of applying an external actuation force on the proximal anchor comprises operating the actuator to move the delivery catheter distally.

47. The method of claim 43 wherein the step of expanding the proximal anchor comprises applying an external actuation force on the proximal anchor.

48. The method of claim 47 wherein the step of applying an external actuation force on the proximal anchor comprises operating the actuator to move the delivery catheter distally.

49. The method of claim 47 wherein the actuator is a first actuator, the step of applying an external actuation force on the proximal anchor comprising operating a second actuator to move a proximal anchor expansion device distally.

50. The method of claim 25 further comprising disengaging the device from a delivery device.

51. The method of claim 50 wherein the disengaging step comprises disengaging a tether from the device.

52. The method of claim 51 wherein the step of disengaging a tether comprises disengaging a hitch wire from the device.

* * * * *